(12) United States Patent
Fuseya et al.

(10) Patent No.: US 11,819,647 B2
(45) Date of Patent: *Nov. 21, 2023

(54) DILATOR

(71) Applicant: ASAHI INTECC CO., LTD., Seto (JP)

(72) Inventors: Yukihiro Fuseya, Seto (JP); Hideaki Maki, Seto (JP); Daiki Takahashi, Seto (JP); Akira Sawai, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/830,621

(22) Filed: Jun. 2, 2022

(65) Prior Publication Data

US 2022/0288365 A1 Sep. 15, 2022

Related U.S. Application Data

(63) Continuation of application No. 16/579,946, filed on Sep. 24, 2019, now Pat. No. 11,389,631, which is a (Continued)

(30) Foreign Application Priority Data

Mar. 24, 2017 (WO) .................. PCT/JP2017/012024

(51) Int. Cl.
*A61M 29/00* (2006.01)
*A61M 25/06* (2006.01)
(Continued)

(52) U.S. Cl.
CPC .......... *A61M 29/00* (2013.01); *A61M 25/008* (2013.01); *A61M 25/0023* (2013.01);
(Continued)

(58) Field of Classification Search
CPC ................ A61B 17/3417; A61B 90/02; A61B 2017/00915; A61B 2017/3456;
(Continued)

(56) References Cited

U.S. PATENT DOCUMENTS 4,848,342 A * 7/1989 Kaltenbach ........... A61M 29/02
606/198
5,098,374 A 3/1992 Othel-Jacobsen et al.
(Continued)

FOREIGN PATENT DOCUMENTS

JP    S60-234671 A    11/1985
JP    2502565 Y    6/1996
(Continued)

OTHER PUBLICATIONS

May 29, 2018 International Search Report issued in International Patent Application No. PCT/JP2018/011674.

*Primary Examiner* — Jocelin C Tanner
(74) *Attorney, Agent, or Firm* — Oliff PLC

(57) ABSTRACT

Provided is a dilator capable of increasing the diameter of a hole formed on the wall of a digestive tract and the like while ensuring distal-end flexibility and maintaining pushability and torquability even when a shaft is longer and curved. A dilator includes a hollow shaft having an outer diameter that is smaller at a distal end than at a proximal end, and a grip portion connected to the proximal end of the shaft. A spirally-arranged protruding portion protruding outwardly is provided on an outer peripheral surface of the shaft. The spirally-arranged protruding portion has gaps between adjacent portions along a longitudinal axis of the shaft.

13 Claims, 8 Drawing Sheets

Related U.S. Application Data continuation of application No. PCT/JP2018/011674, filed on Mar. 23, 2018.

(51) Int. Cl.
*A61M 25/00* (2006.01)
*A61B 17/34* (2006.01)

(52) U.S. Cl.
CPC .... *A61M 25/0052* (2013.01); *A61M 25/0053* (2013.01); *A61M 25/0662* (2013.01); *A61B 2017/3458* (2013.01); *A61M 25/005* (2013.01); *A61M 2025/006* (2013.01); *A61M 2025/0687* (2013.01)

(58) Field of Classification Search
CPC ... A61B 2017/3458; A61B 2090/3966; A61M 25/0023; A61M 25/005; A61M 25/0052; A61M 25/0053; A61M 25/008; A61M 25/0662; A61M 29/00; A61M 2025/006; A61M 2025/0687
See application file for complete search history.

(56) References Cited

U.S. PATENT DOCUMENTS

| | | | |
|---|---|---|---|
| 5,211,636 A | 5/1993 | Mische | |
| 5,303,714 A | 4/1994 | Abele et al. | |
| 5,630,813 A | 5/1997 | Kieturakis | |
| 11,331,459 B2 | 5/2022 | Fuseya et al. | |
| 11,389,631 B2 * | 7/2022 | Fuseya | A61M 29/00 |
| 2001/0052721 A1 | 12/2001 | Tanaka | |
| 2002/0077655 A1 * | 6/2002 | Frova | A61M 16/0472 |
| | | | 606/196 |
| 2003/0069522 A1 | 4/2003 | Jacobsen et al. | |
| 2005/0022585 A1 | 2/2005 | Berkman | |
| 2005/0165405 A1 | 7/2005 | Tsou | |
| 2006/0235455 A1 | 10/2006 | Oshida | |
| 2007/0088230 A1 | 4/2007 | Terashi et al. | |
| 2008/0097247 A1 | 4/2008 | Eskuri | |
| 2009/0005814 A1 | 1/2009 | Miller et al. | |
| 2009/0281500 A1 | 11/2009 | Acosta et al. | |
| 2010/0076264 A1 * | 3/2010 | Tallarida | A61M 25/0068 |
| | | | 600/137 |
| 2011/0098531 A1 | 4/2011 | To | |
| 2011/0144681 A1 | 6/2011 | Whitman et al. | |
| 2011/0213316 A1 | 9/2011 | Ibrahim et al. | |
| 2011/0270191 A1 * | 11/2011 | Paul | A61B 17/3403 |
| | | | 604/164.1 |
| 2012/0004606 A1 | 1/2012 | Lentz | |
| 2012/0029281 A1 | 2/2012 | Frassica et al. | |
| 2012/0116350 A1 | 5/2012 | Strauss et al. | |
| 2012/0265100 A1 | 10/2012 | Maki | |
| 2012/0310217 A1 | 12/2012 | Maki | |
| 2013/0090523 A1 | 4/2013 | Van Bladel et al. | |
| 2013/0274782 A1 | 10/2013 | Morgan | |
| 2014/0046357 A1 * | 2/2014 | Neoh | A61M 29/00 |
| | | | 606/191 |
| 2015/0094543 A1 | 4/2015 | Whittaker et al. | |
| 2016/0024343 A1 | 1/2016 | Nakai et al. | |
| 2016/0287849 A1 | 10/2016 | Hodson | |
| 2017/0296221 A1 | 10/2017 | Di Caprio et al. | |
| 2019/0001456 A1 | 1/2019 | Kalhori et al. | |
| 2020/0016385 A1 | 1/2020 | Fuseya et al. | |
| 2020/0016386 A1 | 1/2020 | Fuseya et al. | |
| 2020/0016387 A1 | 1/2020 | Fuseya et al. | |
| 2021/0001097 A1 | 1/2021 | Fuseya et al. | |

FOREIGN PATENT DOCUMENTS

| | | |
|---|---|---|
| JP | 2000-057852 A | 2/2000 |
| JP | 2001-286963 A | 10/2001 |
| JP | 2002-177289 A | 6/2002 |
| JP | 2004-009844 A | 1/2004 |
| JP | 2005-118102 A | 5/2005 |
| JP | 2006-130073 A | 5/2006 |
| JP | 2007-501102 A | 1/2007 |
| JP | 2007-098120 A | 4/2007 |
| JP | 2008-011867 A | 1/2008 |
| JP | 2010-540072 A | 12/2010 |
| JP | 2012-095812 A | 5/2012 |
| JP | 2012-100827 A | 5/2012 |
| JP | 2012-179222 A | 9/2012 |
| JP | 2012-183125 A | 9/2012 |
| JP | 2014-136047 A | 7/2014 |
| JP | 2014-524807 A | 9/2014 |
| JP | 5991951 B2 | 9/2016 |
| JP | 2017-051328 A | 3/2017 |
| JP | 2017-523019 A | 8/2017 |
| JP | 2018-033985 A | 3/2018 |
| JP | 2019-507021 A | 3/2019 |
| WO | 91/07202 A1 | 5/1991 |
| WO | 2004/066827 A3 | 8/2004 |
| WO | 2009/045276 A1 | 4/2009 |
| WO | 2010/123825 A1 | 10/2010 |
| WO | 2013/038720 A1 | 3/2013 |
| WO | 2015/032727 A1 | 3/2015 |
| WO | 2016/018434 A1 | 2/2016 |
| WO | 2018-180209 A1 | 10/2018 |

* cited by examiner

DILATOR

CROSS REFERENCE TO RELATED APPLICATIONS

This is a continuation of application Ser. No. 16/579,946 filed Sep. 24, 2019, which is a continuation of PCT/JP2018/011674, filed Mar. 23, 2018, which claims priority to PCT/JP2017/012024, filed Mar. 24, 2017. The contents of these applications are incorporated herein by reference in their entirety.

BACKGROUND

The present disclosure relates to a dilator.

Conventionally, an auxiliary tool called a sheath introducer is used when a catheter is inserted into a body lumen such as a patient's blood vessel. A sheath introducer includes a sheath for connecting a patient's body lumen to the outside of the body, and a dilator to be inserted into the sheath for expanding a hole formed on a body surface. For example, Japanese Patent Application Laid-Open Publication No. 2008-11867 describes a sheath introducer 200 including a sheath 80 and a dilator 70 (see FIG. 1 and others).

The above sheath introducer 200 is used as follows: the patient's skin is first perforated at a predetermined location using an introducer needle, a guide wire is inserted into a body lumen such as a blood vessel through the resulting hole, a proximal end of the guide wire is inserted into a distal end of the sheath introducer 200 where the dilator 70 is already inserted into the sheath 80, and the sheath introducer 200 is then inserted into the body lumen along the guide wire. During this, a distal end of the dilator 70 will expand the diameter of the hole formed on the skin. Subsequently, the dilator 70 is withdrawn from the sheath introducer 200, and then a catheter is inserted into the sheath introducer 200 and is inserted into a body lumen such as a blood vessel.

Such a sheath introducer is usually designed to be inserted through the patient's skin, and is generally short and linear as described in Japanese Patent Application Laid-Open Publication No. 2008-11867. Meanwhile, an alternative procedure is performed as follows: an introducer needle is pushed out of a distal end of an endoscope inserted through the patient's mouth or nose instead of through the patient's skin to perforate the wall of a digestive tract such as a patient's stomach at a predetermined location, a guide wire is inserted through the resulting hole, a proximal end of the guide wire is inserted into a distal end of a dilator, and the dilator is then inserted into the wall of the digestive tract along the guide wire to increase the diameter of the hole formed on the wall of the digestive tract.

A dilator for use in such a procedure is designed to be inserted through the patient's mouth or nose, and thus needs to be relatively long and generally configured so as to be used in a curved state, considering that it is to be passed through the digestive tract.

However, an increased length of a dilator may have a problem in that a rotational force (torque) and pushing force (pushability) from the user's hand cannot be transmitted to a distal end of the dilator, which in turn may preclude increasing the diameter of a hole formed on the wall of a digestive tract. In particular, a curved dilator further had a problem in that the deterioration of these properties becomes more significant.

SUMMARY

The disclosed embodiments have been devised in view of these circumstances. An object of the disclosed embodiments is to provide a dilator capable of easily increasing the diameter of a hole formed on the wall of a digestive tract and the like and also capable of maintaining pushability and torquability even when a shaft is longer and curved.

In order to achieve the above object, provided is a dilator including: a hollow shaft having an outer diameter that is smaller at a distal end of the shaft than at a proximal end of the shaft; and a grip portion connected to the proximal end of the shaft, a spirally-arranged protruding portion protruding outwardly being provided on an outer peripheral surface of the shaft, and the spirally-arranged protruding portion having gaps between adjacent protruding portions along a longitudinal axis of the shaft.

DETAILED DESCRIPTION OF EMBODIMENTS

Below, the embodiments of the present disclosure will be described with reference to the figures. It is noted that the dimensions of the dilators shown in the figures are merely provided to facilitate understanding of the embodiments, and do not necessarily correspond to the actual dimensions.

Figure 1:
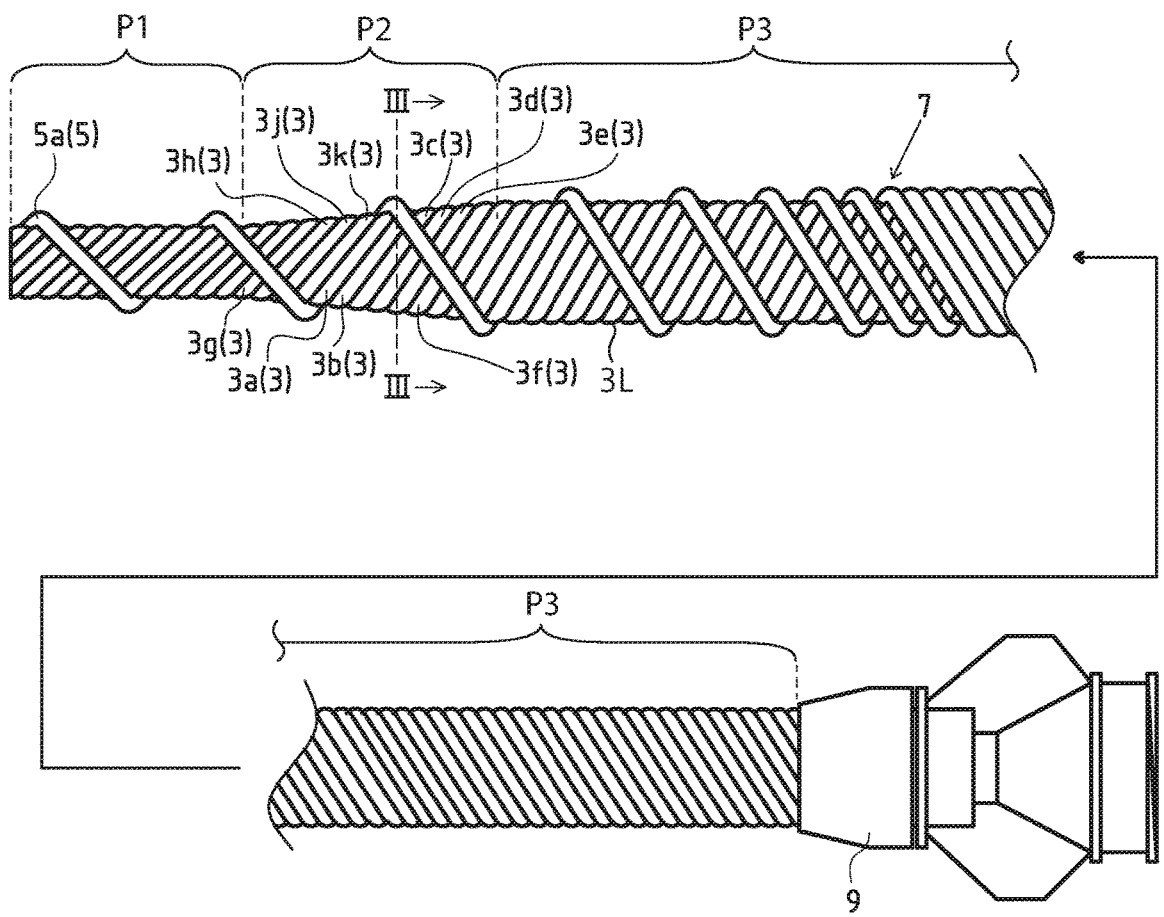
FIG. 1 show an overall view of a dilator according to the disclosed embodiments.
Figure 2:
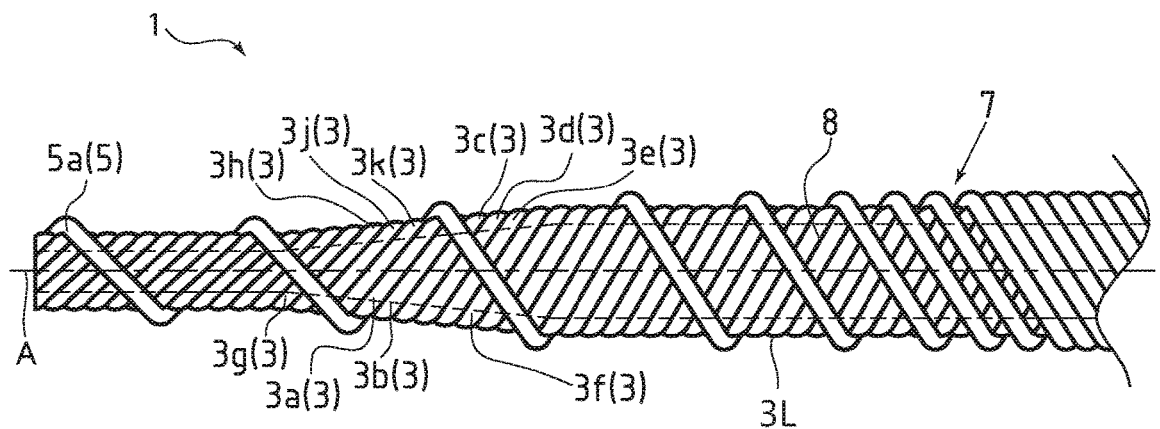
FIG. 2 shows a distal end portion with a view of an inner cavity of the dilator (a multilayer body) shown in FIG. 1.
Figure 3:
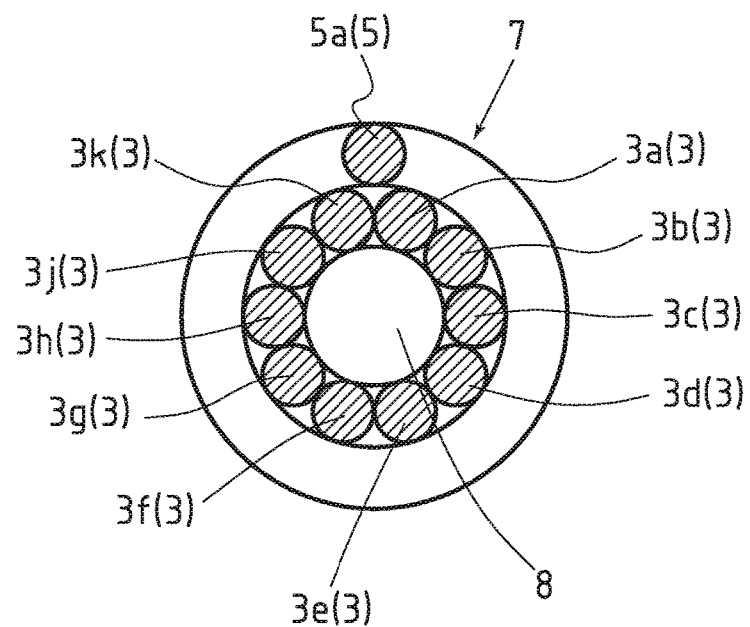
FIG. 3 shows a cross-sectional view taken along line III-III in FIG. 1.

FIG. 1 shows an overall view of a dilator according to the disclosed embodiments, FIG. 2 shows a front end portion (distal end portion) with a view of an inner cavity of the dilator (a multilayer body), and FIG. 3 shows a cross-sectional view taken along line III-III in FIG. 1.

In FIGS. 1 and 2, the left side in the figure corresponds to the front end side (the distal side) which is to be inserted into the body, and the right side corresponds to the base end side (the hand side, the proximal side) which is to be operated by an operator such as a surgeon.

In FIG. 1, a dilator 1 includes: a multilayer body 7 including a hollow coil body 3 including a plurality of element wires 3a, 3b, 3c, 3d, 3e, 3f, 3g, 3h, 3j, and 3k (e.g., metal wires) wound around into a hollow shape, and a coil body 5 including a single element wire 5a (e.g., a metal wire) wound around a surface of the hollow coil body 3 in a direction (clockwise, facing to the distal end) opposite to the hollow coil body 3 (counterclockwise, facing to the distal end); and a connector 9 having a hollow shape connected to a proximal end of the multilayer body 7.

Here, the multilayer body 7 has a cylindrical hollow shape at a proximal end portion P3, has a tapered hollow shape at an intermediate portion P2, and has a cylindrical hollow shape at a distal end portion P1.

It is noted that the wires 3a, 3b, 3c, 3d, 3e, 3f, 3g, 3h, 3j, and 3k correspond to the "first wires," and the hollow coil body 3 corresponds to the "first layer body," the "shaft," and the "first coil."

In addition, the wire 5a corresponds to the "second wire," and the coil body 5 corresponds to the "second layer body," the "spirally-arranged protruding portion," and the "second coil."

Further, the intermediate portion P2 of the hollow coil body 3 corresponds to the "tapered hollow portion" and the "portion having an increasing outer diameter (tapered shape)." Further, the connector 9 corresponds to the "grip portion."

The hollow coil body 3 is configured such that the wires 3a, 3b, 3c, 3d, 3e, 3f, 3g, 3h, 3j, and 3k are 10 wires (e.g., stainless steel wires) wound around into a hollow shape as shown in FIG. 3. The hollow coil body 3 has a cylindrical hollow shape at the proximal end portion P3, has a tapered hollow shape at the intermediate portion P2, has a cylindrical hollow shape at the distal end portion P1, and has an outer diameter increasing toward a proximal end (an increasing outer diameter). That is, the hollow coil body 3 has a hollow shape having an outer diameter that is smaller at the distal end than at the proximal end.

In FIG. 2, the dotted lines represent the common inscribed lines of the hollow coil body 3. An inner cavity 8 is formed in the inner side of the common inscribed lines of the hollow coil body 3 (see FIG. 3).

It is noted that, while wires made of stainless steel can be used as the wires of the hollow coil body 3, they are not limited to stainless steel wires. They may be wires made of a superelastic alloy such as nickel-titanium. Further, they are not limited to metal wires and may be resin wires.

The coil body 5 is configured such that a wire 5a (e.g., a stainless steel wire) is wound around in a direction (clockwise, facing to the distal end) opposite to the hollow coil body 3 (counterclockwise, facing to the distal end). Here, the wire 5a is wound around closely (with a small winding pitch, for example where adjacent windings of the wire 5a are in contact with each other) at the proximal end side and is wound around with gaps between adjacent windings at the intermediate portion P2 and the distal end portion P1. The coil body 5 provides a spirally-arranged protruding portion protruding outwardly (the outermost surface of the dilator 1, the outermost portion) on an outer peripheral surface 3L of the hollow coil body 3. The spirally-arranged protruding portion extends in a spiral shape along its length, and has gaps between adjacent portions (adjacent windings of the wire 5a) along a longitudinal A of the hollow coil body 3.

Further, the coil body 5 is provided at the intermediate portion P2, which corresponds to a portion having an increasing outer diameter of the hollow coil body 3.

Further, the amount of gap (space) between adjacent windings of the wire 5a (i.e., the distance between adjacent windings in the longitudinal direction) is gradually decreased at the proximal end portion P3 toward the proximal end side thereof. This configuration enables the stiffness of the dilator 1 (the multilayer body 7) to be gradually changed along an axis direction (a direction of the longitudinal axis) so that the dilator 1 (multilayer body 7) can easily enter into the inside of an approach pathway even when the approach pathway meanders.

It is noted that the wire 5a is configured such that the amount of gap between adjacent windings of the wire 5a is gradually decreased at the proximal end portion P3 toward the proximal end side thereof, but the configuration shall not be limited to this. Even when the amount of gap between adjacent windings of the wire 5a is constant from the distal end portion P1 toward the proximal end portion P3, the distal-end flexibility of the dilator 1 (multilayer body 7) can be ensured, and the pushability and torquability of the dilator 1 (multilayer body 7) can be maintained in a case where the dilator 1 (multilayer body 7) is longer and curved. Further, the screw effect of the single wire 5a enables the dilator 1 to be advanced not only by a pushing operation but also by a rotational operation. Further, the diameter of a pre-formed hole can easily be increased by the coil body 5 provided at a portion where the hollow coil body 3 has an increasing outer diameter, i.e., at the intermediate portion P2.

Further, with regard to the wire 5a, the amount of gap between adjacent windings of the wire 5a is gradually decreased at the proximal end portion P3 toward the proximal end side thereof. This configuration can have the following effect: the stiffness of the dilator 1 (the multilayer body 7) in the axis direction can be gradually changed so that the dilator 1 (multilayer body 7) can easily enter into the inside of an approach pathway even when the approach pathway meanders.

Further, a shaft composed of the hollow coil body 3 (the first coil) including a plurality of wires wound around into a hollow shape can improve the flexibility of the shaft and the transmissibility of torque via the shaft. Further, a spirally-arranged protruding portion composed of the coil body 5 (the second coil) including the single wire 5a wound around on the outer peripheral surface 3L of the hollow coil body 3 can easily be formed, can ensure the flexibility of the distal end of the dilator 1, and can improve the torquability by virtue of the elasticity of the second coil. Further, each wire of the hollow coil body 3 is wound around in a direction opposite to the wire 5a of the coil body 5. Therefore, even when the dilator 1 is rotated in a direction to open the hollow coil body 3, a force is applied in a direction to close the coil body 5 to prevent the opening of the hollow coil body 3. This allows a force applied to the connector 9 of the dilator 1 to be transmitted to the distal end side.

It is noted that the wire 5a can be made of stainless steel, but the material shall not be limited to stainless steel. A metal wire made of a superelastic alloy such as nickel-titanium may be used. Further, it shall not be limited to a metal wire, and a resin wire may be used.

The length of the dilator is, for example, 2000 mm, preferably 1600 mm to 2500 mm; the length of the distal end portion P1 is, for example, 10 mm, preferably 0 mm to 100 mm; and the length of the intermediate portion P2 is, for example, 30 mm, preferably 5 mm to 100 mm. The inner diameter of the hollow coil body 3 at the distal end is, for example, 0.7 mm, preferably 0.4 mm to 1.0 mm, and the inner diameter of the hollow coil body 3 at the proximal end is, for example, 1.5 mm, preferably 1.0 mm to 3.0 mm. The outer diameter of the coil body 5 at the distal end is, for example, 1.84 mm, preferably 0.8 mm to 3.0 mm, and the outer diameter of the coil body 5 at the proximal end is, for example, 2.64 mm, preferably 1.4 mm to 5.0 mm. Further, the diameters of the wires 3*a* to 3*h* and 3*j* to 3*k* are, for example, 0.21 mm, preferably 0.1 mm to 0.5 mm, and the diameter of the wire 5*a* is, for example, 0.36 mm, preferably 0.1 mm to 0.5 mm.

The distal end of the connector 9 is connected to the proximal end of the hollow coil body 3 and the proximal end of the coil body 5. The connector 9 is made of a resin and has a hollow shape which has an inner cavity communicating with the inner cavity 8 of the hollow coil body 3.

Next, an example of an operating mode of the above dilator will be described.

First, a target object is punctured using an introducer needle. After the puncture, a guide wire is inserted through an inner cavity of the introducer needle, and the introducer needle is withdrawn thereafter. Then, the distal end of the dilator 1 is inserted from the proximal end of the guide wire into the punctured portion. Subsequently, the diameter of a hole at the punctured portion can be increased by pushing and rotating the dilator 1 inward.

Figure 4:
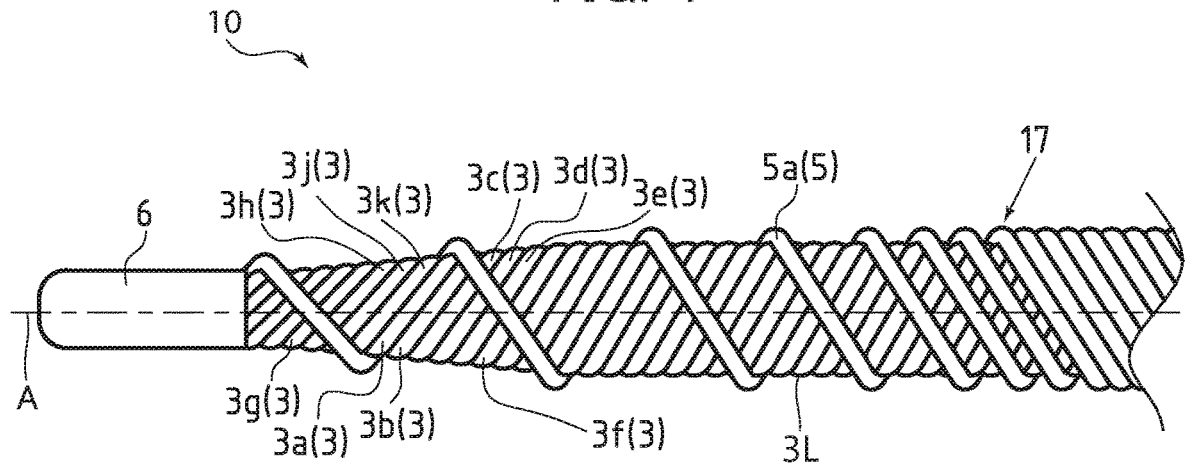
FIG. 4 shows a distal end portion of a dilator (a multilayer body) according to the disclosed embodiments.

FIG. 4 shows a distal end portion of a dilator (a multilayer body) according to the disclosed embodiments. In FIG. 4, the left side in the figure corresponds to the front end side (the distal side) which is to be inserted into the body, and the right side corresponds to the base end side (the hand side, the proximal side) which is to be operated by an operator such as a surgeon.

It is noted that the dilator in FIG. 4 basically has the same structure as the dilator 1 in FIGS. 1-3. Therefore, the same number is given to the same member, and a detailed description will be omitted.

In FIG. 4, a dilator 10 includes: a multilayer body 17 including the hollow coil body 3 including the plurality of wires 3*a*, 3*b*, 3*c*, 3*d*, 3*e*, 3*f*, 3*g*, 3*h*, 3*j*, and 3*k* wound around into a hollow shape, the coil body 5 including the single wire 5*a* wound around the surface of the hollow coil body 3 in a direction (clockwise, facing to the distal end) opposite to the hollow coil body 3 (counterclockwise, facing to the distal end); and a connector 9 having a hollow shape and being connected to the proximal end of the multilayer body 17. However, the dilator 10 differs from the dilator 1 in that the multilayer body 17 of the dilator 10 has a distal-end portion 6 at the distal end of the hollow coil body 3 while the multilayer body 7 of the dilator 1 does not. The hollow coil body 3 having the distal-end portion 6 provided at the distal end corresponds to the "shaft."

The distal-end portion 6 is formed by casting a solder material (a silver-tin solder material, a gold-tin solder material, or the like) into the distal end of the hollow coil body 3 and has a substantially cylindrical hollow shape. Further, the surface of the distal-end portion 6 is flat (smooth) while the surface of the distal end of the multilayer body 7 is uneven.

The dilator 10 having the aforementioned configuration in which the distal-end portion 6 having a flat surface is connected to the distal end of the multilayer body 17 can further improve insertability into a punctured portion by first pressing the dilator against the punctured portion, and then pushing and rotating the dilator thereinto.

Figure 5:
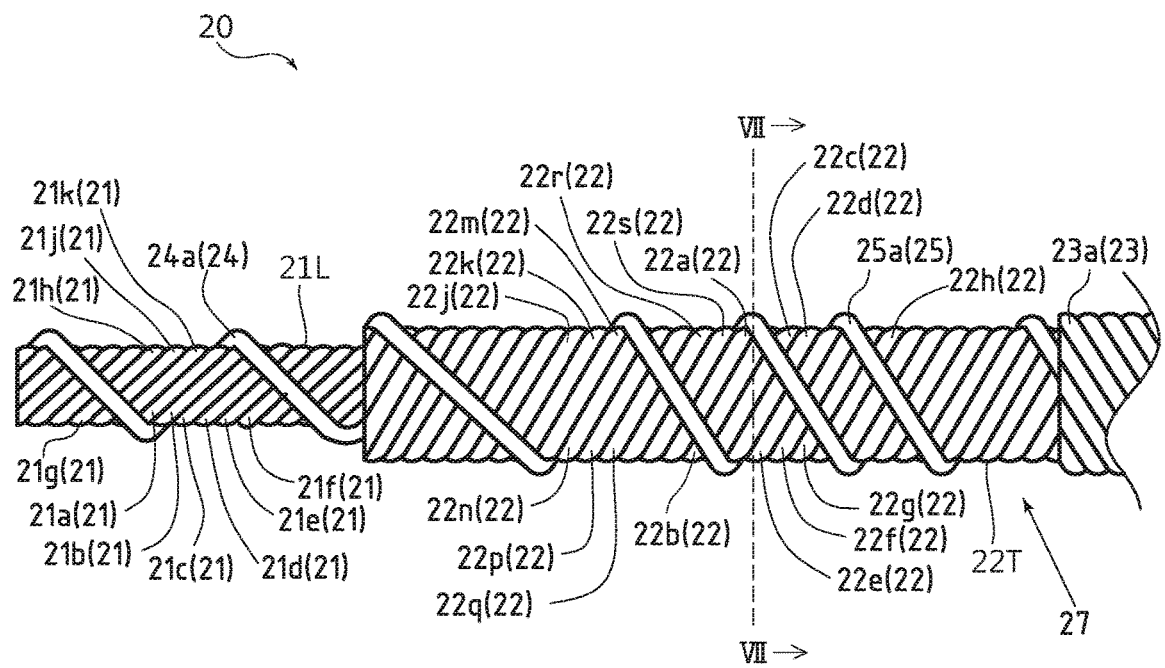
FIG. 5 shows a distal end portion of a dilator (a multilayer body) according to the disclosed embodiments.
Figure 6:
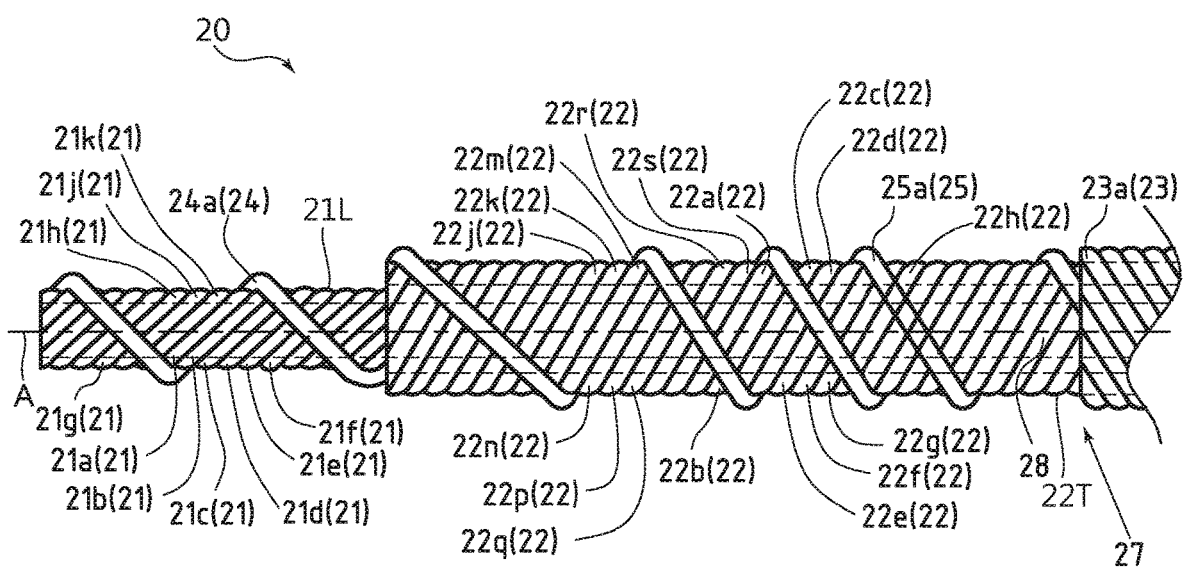
FIG. 6 shows a distal end portion with a view of an inner cavity of the dilator (a multilayer body) shown in FIG. 5.
Figure 7:
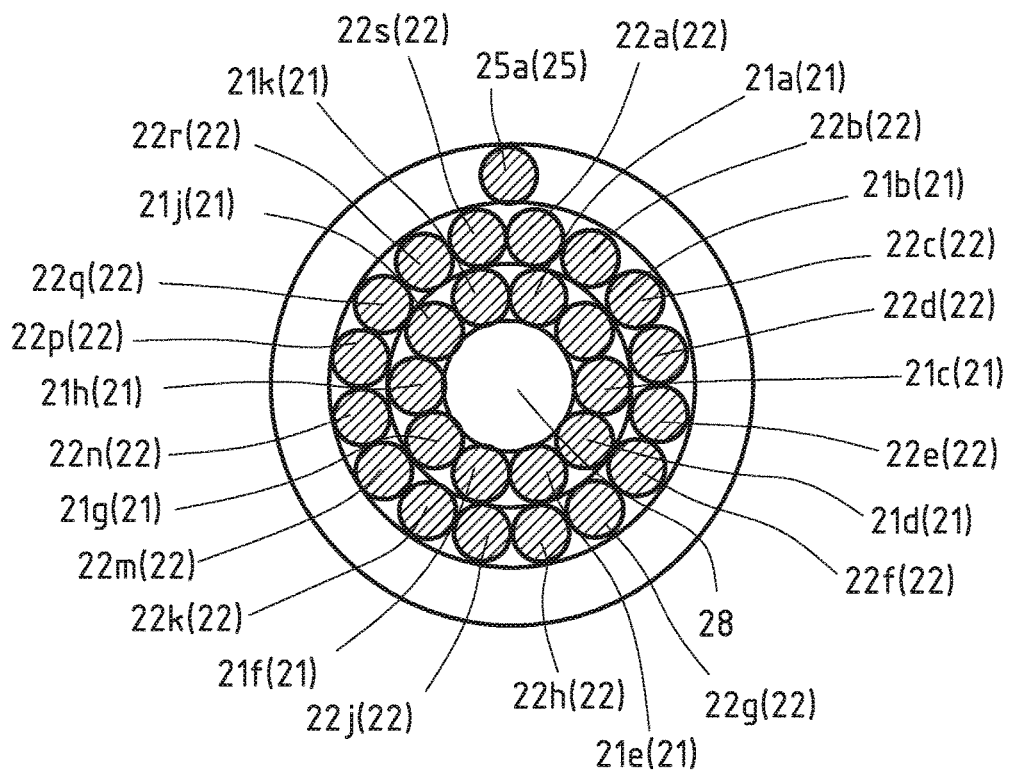
FIG. 7 shows a cross-sectional view taken along line VII-VII in FIG. 5.

FIG. 5 shows a distal end portion of a dilator (a multilayer body) according to the disclosed embodiments, FIG. 6 shows the distal end portion with a view of an inner cavity of the dilator, and FIG. 7 shows a cross-sectional view taken along line VII-VII in FIG. 5.

In FIGS. 5 and 6, the left side in the figure corresponds to the front end side (the distal side) which is to be inserted into the body, and the right side corresponds to the base end side (the hand side, the proximal side) which is to be operated by an operator such as a surgeon.

In FIG. 5, a dilator 20 includes: a multilayer body 27 including a hollow coil body 21 including a plurality of wires 21*a*, 21*b*, 21*c*, 21*d*, 21*e*, 21*f*, 21*g*, 21*h*, 21*j*, and 21*k* wound around into a hollow shape; a coil body 22 proximally spaced from a distal end of the hollow coil body 21 and including a plurality of wires 22*a*, 22*b*, 22*c*, 22*d*, 22*e*, 22*f*, 22*g*, 22*h*, 22*j*, 22*k*, 22*m*, 22*n*, 22*p*, 22*q*, 22*r*, and 22*s* wound around on an outer periphery of the hollow coil body 21 in the same direction (counterclockwise, facing to the distal end) as the hollow coil body 21; a coil body 23 proximally spaced from a distal end of the coil body 22 and including a plurality of wires 23*a* (only one of the wires 23*a* is indicated by a reference number in FIGS. 5 and 6) wound around on an outer periphery of the coil body 22 in a direction (clockwise, facing to the distal end) opposite to the coil body 22 (counterclockwise, facing to the distal end); a coil body 25 including a single wire 25*a* wound around with gaps between adjacent windings on the outer periphery of the coil body 22 in a region distal to a distal end of the coil body 23; and a coil body 24 including a single wire 24*a* wound around (in the same direction as the wire 25*a*) with gaps between adjacent windings on the outer periphery of the coil body 21 in a region distal to a distal end of the coil body 22. The dilator 20 further includes a connector 9 (not shown) having a hollow shape and connected to a proximal end of the multilayer body 27.

Here, the multilayer body 27 has a cylindrical hollow shape at the proximal end side of the proximal end portion P3 as in the multilayer body 7 and the multilayer body 17. However, the multilayer body 27 has a stepped and cylindrical hollow shape in the vicinity of the distal end and intermediate portions while the multilayer body 7 and the multilayer body 17 have intermediate portions with tapered shapes.

It is noted that the wires 21*a*, 21*b*, 21*c*, 21*d*, 21*e*, 21*f*, 21*g*, 21*h*, 21*j*, and 21*k* correspond to the "third wires," and the hollow coil body 21 corresponds to the "third layer body."

Further, the wires 22*a*, 22*b*, 22*c*, 22*d*, 22*e*, 22*f*, 22*g*, 22*h*, 22*j*, 22*k*, 22*m*, 22*n*, 22*p*, 22*q*, 22*r*, and 22*s* corresponds to the "fourth wires," and the coil body 22 corresponds to the "fourth layer body" and the "portion having an increasing outer diameter."

Further, the wire 24*a* corresponds to the "fifth wire," and the coil body 24 corresponds to the "fifth layer body."

Further, the wires 23*a* correspond to the "sixth wires," and the coil body 23 corresponds to the "sixth layer body."

Further, the wire 25*a* corresponds to the "seventh wire," and the hollow coil body 25 corresponds to the "seventh layer body."

The hollow coil body 21 and the coil body 22 together correspond to the "shaft" and the "first coil." The coil body 24 and the coil body 25 together correspond to the "spirally-arranged protruding portion" and the "second coil."

The hollow coil body 21 is configured such that the wires 21*a*, 21*b*, 21*c*, 21*d*, 21*e*, 21*f*, 21*g*, 21*h*, 21*j*, and 21*k* are 10 wires (e.g., stainless steel wires) that are twisted into a hollow shape as shown in FIG. 7. The hollow coil body 21 has a cylindrical hollow shape from the distal end to the connector 9.

In FIG. 6, the dotted line (the innermost among the three dotted lines) represents the common inscribed line of the hollow coil body 21. An inner cavity 28 is formed in the inner side of the common inscribed line of the hollow coil body 21 (see FIG. 7).

Further, the coil body 22 is formed such that the wires 22a, 22b, 22c, 22d, 22e, 22f, 22g, 22h, 22j, 22k, 22m, 22n, 22p, 22q, 22r, and 22s are 16 wires (e.g., stainless steel wires) that are twisted on a surface of the coil body 21 as shown in FIG. 7. The coil body 22 also has a cylindrical hollow shape from the distal end to the connector 9.

In FIG. 6, the dotted line (the intermediate among the three dotted lines) represents the common inscribed line of the coil body 22.

Further, the coil body 23 is formed such that the wires 23a are 23 wires (e.g., stainless steel wires) that are twisted on a surface of the coil body 22. The coil body 23 also has a cylindrical hollow shape from the distal end to the connector 9.

In FIG. 6, the dotted line (the outermost among the three dotted lines) represents the common inscribed line of the hollow coil body 23. The coil body 22 is twistedly formed on the surface of the hollow coil body 21. This means that the shaft formed from the hollow coil body 21 and the coil body 22 has a hollow shape and an outer diameter that is smaller at a distal end than at a proximal end.

Further, the coil body 24 is formed such that the wire 24a (e.g., a stainless steel wire) is wound on the surface of the coil body 21, and the coil body 25 is formed such that the wire 25a (e.g., a stainless steel wire) is wound on the surface of the coil body 22.

Each element wire in the hollow coil body 21, the coil body 22, and the coil body 23 is wound around closely, and in the coil body 24 and the coil body 25, a wire is wound around with gaps between adjacent windings (see FIG. 6). The coil body 24 provides a spirally-arranged protruding portion protruding outwardly (the outermost surface of the dilator 20, the outermost portion) on an outer peripheral surface 21L of the hollow coil body 21, and the coil body 25 provides a spirally-arranged protruding portion protruding outwardly (the outermost surface of the dilator 20, the outermost portion) on an outer peripheral surface 22T of the coil body 22. The spirally-arranged protruding portion has gaps between adjacent portions (adjacent portions of the wire) along an axis A of the hollow coil body 21. Further, the coil body 25 is provided on the coil body 22 as a portion in which the shaft has an increasing outer diameter.

It is noted that metal wires made of stainless steel can be used for the wires of the hollow coil body 21, the coil body 22, the coil body 23, the coil body 24, and the coil body 25, but they are not limited to stainless steel wires. They may be made of a superelastic alloy such as nickel-titanium. Further, they are not limited to metal wires and may be resin wires.

The dilator 20 (the multilayer body 27) can ensure the distal-end flexibility of the dilator 20 (the multilayer body 27) and can maintain the pushability and torquability of the dilator 20 (the multilayer body 27) even when the dilator 20 (the multilayer body 27) is longer and curved. Further, the screw effect of the single wire 24a and the single wire 25a enables the dilator 20 to be advanced not only by a pushing operation but also by a rotational operation. Further, the diameter of a pre-formed hole can easily be increased by the coil body 25 provided at the coil body 22 which corresponds to a portion where the shaft has an increasing outer diameter.

It is noted that when the amounts of gap between adjacent windings of the wire 25a and the wire 24a are configured so as to be gradually reduced toward the proximal end side, the following effect can be observed: the stiffness of the dilator 20 (the multilayer body 27) along the axis direction can be gradually changed so that the dilator 20 (the multilayer body 27) can easily enter into the inside of an approach pathway even when the approach pathway meanders.

Further, the shaft (the first coil) composed of the hollow coil body 21 and the coil body 22 each including a plurality of wires wound around into a hollow shape can improve the flexibility of the shaft and the transmissibility of torque via the shaft. Further, the spirally-arranged protruding portion (the second coil) composed of the coil body 24 including a single wire wound around on the outer peripheral surface 21L of the hollow coil body 21 and the coil body 25 wound around on the outer peripheral surface 22T of the coil body 22 can be easily formed, can ensure the flexibility of the distal end of the dilator 20 by virtue of the elasticity of the second coil, and can improve the torquability. Further, the wires of the hollow coil body 21 and the coil body 22 are wound in a direction opposite to the wires of the coil body 24 and the coil body 25. Therefore, even when the dilator 20 is rotated in a direction to open the hollow coil body 21 and the coil body 22, a force is applied in a direction to close the coil body 24 and the coil body 25 to prevent the opening of the hollow coil body 21 and the coil body 22. This allows a force applied to the connector 9 of the dilator 20 to be transmitted to the distal end side.

Figure 8:
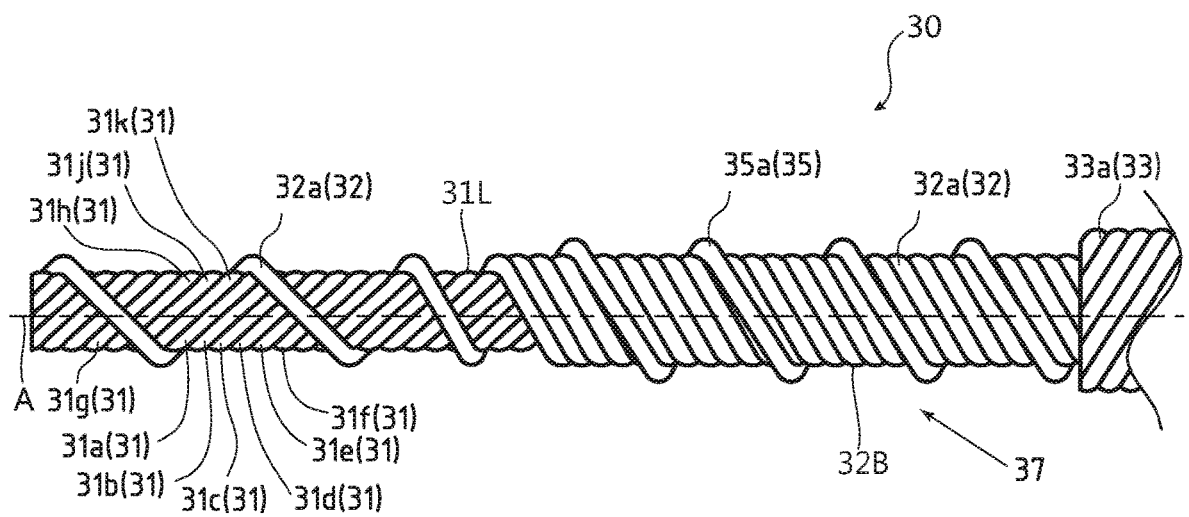
FIG. 8 shows a distal end portion of a dilator (a multilayer body) according to the disclosed embodiments.

FIG. 8 shows a distal end portion of a dilator (a multilayer body) according to the disclosed embodiments. In FIG. 8, the left side in the figure corresponds to the front end side (the distal side) which is to be inserted into the body, and the right side corresponds to the base end side (the hand side, the proximal side) which is to be operated by an operator such as a surgeon.

In FIG. 8, a dilator 30 includes: a multilayer body 37 including a hollow coil body 31 including a plurality of wires 31a, 31b, 31c, 31d, 31e, 31f, 31g, 31h, 31j, and 31k wound around into a hollow shape; a coil body 32 including a single wire 32a wound around on an outer periphery of the hollow coil body 31 from a distal end of the hollow coil body 31 in a direction (clockwise, facing to the distal end) opposite to the hollow coil body 31; a coil body 33 proximally spaced from a distal end of the coil body 32 and including a plurality of wires 33a (only one of the wires 33a is indicated by the reference number in FIG. 8) wound around on an outer periphery of the coil body 32 in a direction (counterclockwise, facing to the distal end) opposite to the coil body 32 (clockwise, facing to the distal end); and a coil body 35 including a single wire 35a wound around with gaps between adjacent windings on the outer periphery of the coil body 32 in a region distal to a distal end of the coil body 33 in the same direction (clockwise, facing to the distal end) as the coil body 32 (clockwise, facing to the distal end). The dilator 30 further includes a connector 9 (not shown) having a hollow shape and being connected to a proximal end of the multilayer body 37.

Here, the multilayer body 37 has a stepped and cylindrical hollow shape as in the multilayer body 27, but it differs from the multilayer body 27 in that the coil body 32 in the multilayer body 37 is formed integrally and continuously while the coil body 22 and the coil body 24 in the multilayer body 27 are formed as separate members. That is, in the coil body 32, the wire 32a is wound around closely at the proximal end side while wound around with gaps between adjacent windings at the distal end side as shown in FIG. 8.

It is noted that the hollow coil body 31 and a portion of the coil body 32 where the wire 32a is wound around closely together correspond to the "shaft" and the "first coil." The coil body 35 and the portion of the coil body 32 where the wire 32a is wound around with gaps between adjacent windings together correspond to the "spirally-arranged protruding portion" and the "second coil." Further, the portion of the coil body 32 where the wire 32a is wound around closely corresponds to the "portion having an increasing outer diameter."

The hollow coil body 31 is formed such that the wires 31a, 31b, 31c, 31d, 31e, 31f, 31g, 31h, 31j, and 31k are 10 wires (e.g., stainless steel wires) that are twisted into a hollow shape as in the hollow coil body 21. The hollow coil body 31 has a cylindrical hollow shape from the distal end to the connector 9.

Further, the coil body 32 is formed such that the wire 32a (e.g., a stainless steel wire) is wound around a surface of the coil body 31. The coil body 32 also has a cylindrical hollow shape from the distal end to the connector 9.

Further, the coil body 33 is formed such that the wires 33a are 23 wires (e.g., stainless steel wires) that are twisted on a surface of the coil body 32. The hollow coil body 33 also has a cylindrical hollow shape from the distal end to the connector 9. A closely wound portion of the coil body 32 is twistedly formed on the surface of the hollow coil body 31. This means that the shaft formed from the hollow coil body 31 and the closely wound portion of the coil body 32 has a hollow shape having an outer diameter that is smaller at a distal end than at a proximal end.

Further, the coil body 35 is formed such that the wire 35a (e.g., a stainless steel wire) is formed on the surface of the coil body 32.

Each wire in the hollow coil body 31 and the coil body 33 is wound around closely (see FIG. 8). The portion of the coil body 32 where the wire is wound around with gaps between adjacent windings provides a spirally-arranged protruding portion protruding outwardly (the outermost surface of the dilator 30, the outermost portion) on an outer peripheral surface 31L of the hollow coil body 31, and the coil body 35 provides a spirally-arranged protruding portion protruding outwardly (the outermost surface of the dilator 30, the outermost portion) on an outer peripheral surface 32B of the closely wound portion of the coil body 32. These spirally-arranged protruding portions each have gaps between adjacent portions (adjacent windings of the wire) along an axis A of the hollow coil body 31. Further, the coil body 35 is provided at the closely wound portion of the coil body 32, which corresponds to a portion where the shaft has an increasing outer diameter.

It is noted that metal wires made of stainless steel can be used for the wires of the hollow coil body 31, the coil body 32, the coil body 33, and the coil body 35, but they are not limited to stainless steel wires. They may be those made of a superelastic alloy such as nickel-titanium. Further, they are not limited to metal wires and may be resin wires.

The dilator 30 (the multilayer body 37) can ensure the distal-end flexibility of the dilator 30 (the multilayer body 37) and can maintain the pushability and torquability of the dilator 30 (the multilayer body 37) even when the dilator 30 (the multilayer body 37) is longer and curved. Further, the screw effect of the single wire 32a and the single wire 35a extending contiguously toward the distal end from the proximal end of the coil body 32 can further be improved when the multilayer body 37 is rotated. This enables the dilator 30 to be easily advanced not only by a pushing operation but also by a rotational operation. In addition, the coil body 35 is provided in the closely wound portion of the coil body 32, which corresponds to a portion where the shaft has an increasing outer diameter. Therefore, the diameter of a pre-formed hole can be increased more easily.

It is noted that when the amounts of gap between adjacent windings of the wire 32a and the wire 35a are configured so as to be gradually reduced toward the proximal end side, the following effect can be observed: the stiffness of the dilator 30 (the multilayer body 37) along the axis direction can be gradually changed so that the dilator 30 (the multilayer body 37) can easily enter into the inside of an approach pathway even when the approach pathway meanders.

Further, a shaft (the first coil) composed of the hollow coil body 31 including a plurality of wires wound around into a hollow shape, and the coil body 32 can improve the flexibility of the shaft and the transmissibility of torque via the shaft. Further, a spirally-arranged protruding portion (the second coil) composed of the coil body 32 including a single wire wound around the outer peripheral surface 31L of the hollow coil body 31 and the coil body 35 wound around the outer peripheral surface 32B of the coil body 32 can be easily formed, can ensure the flexibility of the distal end of the dilator 30 by virtue of the elasticity of the second coil, and can improve the torquability. Further, the wires of the hollow coil body 31 are wound in a direction opposite to the wires of the coil body 32 and the coil body 35. Therefore, even when the dilator 30 is rotated in a direction to open the hollow coil body 31, a force is applied in a direction to close the coil body 32 and the coil body 35 to prevent the opening of the hollow coil body 31. This allows a force applied to the connector 9 of the dilator 30 to be transmitted to the distal end side.

Figure 9:
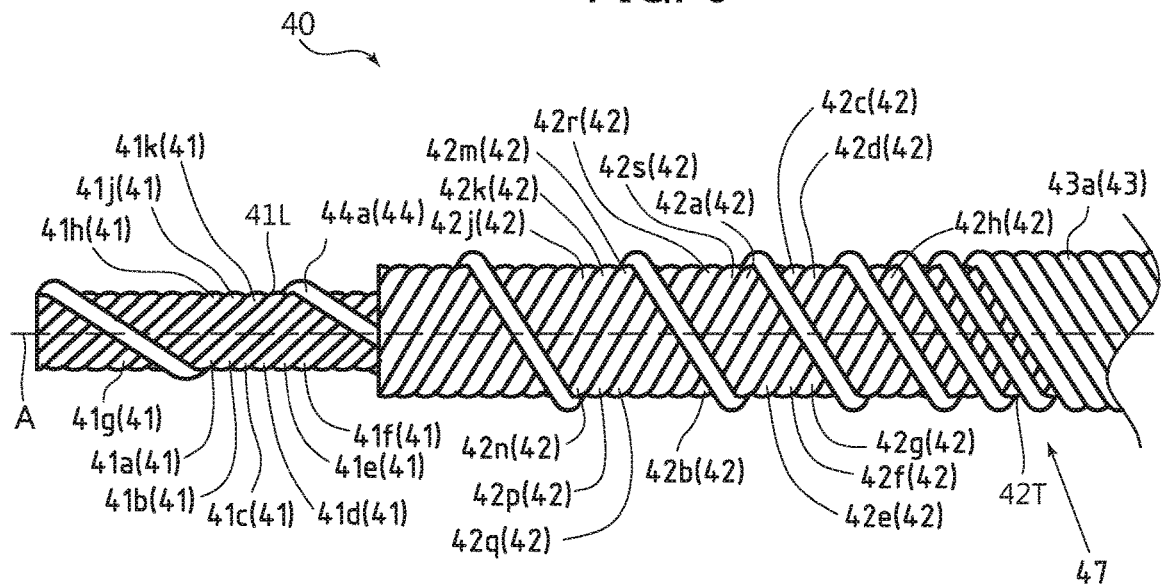
FIG. 9 shows a distal end portion of a dilator (a multilayer body) according to the disclosed embodiments.

FIG. 9 shows a distal end portion of a dilator (a multilayer body) according to the disclosed embodiments.

In FIG. 9, the left side in the figure corresponds to the front end side (the distal side) which is to be inserted into the body, and the right side corresponds to the base end side (the hand side, the proximal side) which is to be operated by an operator such as a surgeon.

In FIG. 9, a dilator 40 includes: a multilayer body 47 including a hollow coil body 41 including a plurality of wires 41a, 41b, 41c, 41d, 41e, 41f, 41g, 41h, 41j, and 41k wound around into a hollow shape; a coil body 42 proximally spaced from a distal end of the hollow coil body 41 and including a plurality of wires 42a, 42b, 42c, 42d, 42e, 42f, 42g, 42h, 42j, 42k, 42m, 42n, 42p, 42q, 42r, and 42s wound around on an outer periphery of the hollow coil body 41 in the same direction (counterclockwise, facing to the distal end) as the hollow coil body 21 (counterclockwise, facing to the distal end); a coil body 43 including a single wire 43a wound around on an outer periphery of the coil body 42 from a distal end of the coil body 42 in a direction (clockwise, facing to the distal end) opposite to the coil body 42; and a coil body 44 including a single wire 44a wound around with gaps between adjacent windings on the outer periphery of the coil body 41 in a region distal to a distal end of the coil body 42 in the same direction (clockwise, facing to the distal end) as the coil body 43 (clockwise, facing to the distal end). The dilator 40 further includes a connector 9 (not shown) having a hollow shape and connected to a proximal end of the multilayer body 47.

Here, the multilayer body 47 has a stepped and cylindrical hollow shape as in the multilayer body 27, but it differs from the multilayer body 27 in that the coil body 43 in the multilayer body 47 is formed integrally and continuously while the coil body 25 and the coil body 23 in the multilayer body 27 are formed as separate members. That is, in the coil body 43, the wire 43a is wound around closely at the proximal end side while wound around with gaps between adjacent windings at the distal end side as shown in FIG. 9.

It is noted that the hollow coil body 41 and the coil body 42 together correspond to the "shaft" and the "first coil." A portion of the coil body 43 wound around closely and the coil body 44 together correspond to the "spirally-arranged protruding portion" and the "second coil." Further, the coil body 42 corresponds to the "portion having an increasing outer diameter."

The hollow coil body 41 is formed such that the wires 41a, 41b, 41c, 41d, 41e, 41f, 41g, 41h, 41j, and 41k are 10 wires (e.g., stainless steel wires) that are twisted into a hollow shape as in the hollow coil body 21. The hollow coil body 41 has a cylindrical hollow shape from the distal end to the connector 9.

Further, the coil body 42 is formed such that the wires 42a, 42b, 42c, 42d, 42e, 42f, 42g, 42h, 42j, 42k, 42m, 42n, 42p, 42q, 42r, and 42s are 16 wires (e.g., stainless steel wires) that are wound around on a surface of the coil body 41 in the same direction (counterclockwise, facing to the distal end) as the hollow coil body 41. The coil body 42 also has a cylindrical hollow shape from the distal end to the connector 9.

Further, the coil body 43 is formed such that the wire 43a (e.g., a stainless steel wire) is wound around on a surface of the coil body 42. The hollow coil body 43 also has a cylindrical hollow shape from the distal end to the connector 9.

Further, the coil body 44 is formed such that the wire 44a (e.g., a stainless steel wire) is wound around the surface of the coil body 41 in the same direction (clockwise, facing to the distal end) as the coil body 43 (clockwise, facing to the distal end).

Each wire in the hollow coil body 41 and the coil body 42 is wound around closely (see FIG. 9). The coil body 42 is twistedly formed on the surface of the hollow coil body 41. This means that the shaft formed by the hollow coil body 41 and the coil body 42 has a hollow shape having an outer diameter that is smaller at a distal end than at a proximal end. The coil body 44 provides a spirally-arranged protruding portion protruding outwardly (the outermost surface of the dilator 40, the outermost portion) on an outer peripheral surface 41L of the hollow coil body 41, and the coil body 43 provides a spirally-arranged protruding portion protruding outwardly (the outermost surface of the dilator 40, the outermost portion) on an outer peripheral surface 42T of the coil body 42. These spirally-arranged protruding portions each have gaps between adjacent portions (adjacent windings of the wire) along an axis A of the hollow coil body 41. Further, the coil body 43 is provided on the coil body 42, which corresponds to a portion where the shaft has an increasing outer diameter.

It is noted that metal wires made of stainless steel can be used for the wires of the hollow coil body 41, the coil body 42, the coil body 43, and the coil body 44, but they are not limited to stainless steel wires. They may be made of a superelastic alloy such as nickel-titanium. Further, they are not limited to metal wires and may be resin wires.

The dilator 40 (the multilayer body 47) can ensure the distal-end flexibility of the dilator 40 (the multilayer body 47) and can maintain the pushability and torquability of the dilator 40 (the multilayer body 47) even when the dilator 40 (the multilayer body 47) is longer and curved. Further, the screw effect of the single wire 43a and the single wire 44a extending contiguously toward the distal end from the proximal end of the coil body 43 can further be improved when the multilayer body 47 is rotated. This enables the dilator 40 to be easily advanced not only by a pushing operation but also by a rotational operation. In addition, the diameter of a pre-formed hole can be increased more easily by the coil body 43 provided at the coil body 42 which corresponds to a portion where the shaft has an increasing outer diameter.

It is noted that when the amounts of gap between adjacent windings of the wire 44a and the wire 43a are configured so as to be gradually reduced toward the proximal end side, the following effect can be observed: the stiffness of the dilator 40 (the multilayer body 47) along the axis direction can be gradually changed so that the dilator 40 (the multilayer body 47) can easily enter into the inside of an approach pathway even when the approach pathway meanders.

Further, a shaft (the first coil) composed of the hollow coil body 41 and the coil body 42 each including a plurality of wires wound around into a hollow shape can improve the flexibility of the shaft and the transmissibility of torque via the shaft. Further, a spirally-arranged protruding portion (the second coil) composed of the coil body 44 including a single wire wound around on the outer peripheral surface 41L of the hollow coil body 41 and the coil body 43 wound around on an outer peripheral surface 42T of the coil body 42 can be easily formed, can ensure the flexibility of the distal end of the dilator 40 by virtue of the elasticity of the second coil, and can improve the torquability. Further, of the wires of the hollow coil body 41 and the coil body 42 are wound in a direction opposite to the wires of the coil body 43 and the coil body 44. Therefore, even when the dilator 40 is rotated in a direction to open the hollow coil body 41 and the coil body 42, a force is applied in a direction to close the coil body 43 and the coil body 44 to prevent the opening of the hollow coil body 41 and the coil body 42. This allows a force applied to the connector 9 of the dilator 40 to be transmitted to the distal end side.

Figure 10:
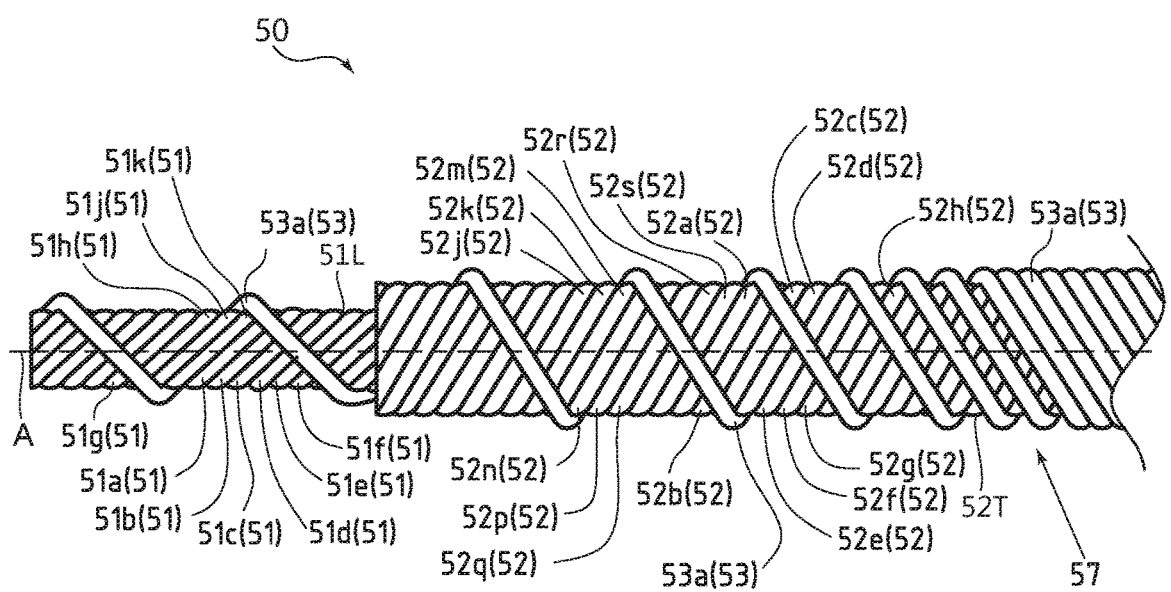
FIG. 10 shows a distal end portion of a dilator (a multilayer body) according to the disclosed embodiments.

FIG. 10 shows a distal end portion of a dilator (a multilayer body) according to the disclosed embodiments.

In FIG. 10, the left side in the figure corresponds to the front end side (the distal side) which is to be inserted into the body, and the right side corresponds to the base end side (the hand side, the proximal side) which is to be operated by an operator such as a surgeon.

In FIG. 10, a dilator 50 includes: a multilayer body 57 including a hollow coil body 51 including a plurality of wires 51a, 51b, 51c, 51d, 51e, 51f, 51g, 51h, 51j, and 51k wound around into a hollow shape; a coil body 52 proximally spaced from a distal end of the hollow coil body 51 and including a plurality of element wires 52a, 52b, 52c, 52d, 52e, 52f, 52g, 52h, 52j, 52k, 52m, 52n, 52p, 52q, 52r, and 52s wound around on an outer periphery of the hollow coil body 51 in the same direction (counterclockwise, facing to the distal end) as the hollow coil body 51 (counterclockwise, facing to the distal end); and a coil body 53 including a single wire 53a wound around on the outer peripheries of the hollow coil body 51 and the coil body 52 from the distal end of the hollow coil body 51 in a direction (clockwise, facing to the distal end) opposite to the hollow coil body 52. The dilator 50 further includes a connector 9 (not shown) having a hollow shape and connected to a proximal end of the multilayer body 57.

Here, the multilayer body 57 has a stepped and cylindrical hollow shape as in the multilayer body 27, but it differs from the multilayer body 27 in that the coil body 53 in the multilayer body 57 is formed integrally and continuously while the coil body 24, the coil body 25, and the coil body 23 in the multilayer body 27 are formed as separate members. That is, in the coil body 53, the single wire 53a is wound around closely at the proximal end side and wound around with gaps between adjacent windings at the distal end side of the coil body 52 and the distal end side of the coil body 51.

It is noted that the hollow coil body 51 and the coil body 52 together correspond to the "shaft" and the "first coil." The portion of the coil body 53 wound around with gaps between adjacent windings corresponds to the "spirally-arranged protruding portion" and the "second coil." Further, the coil body 52 corresponds to the "portion having an increasing outer diameter."

The hollow coil body 51 is formed such that the wires 51a, 51b, 51c, 51d, 51e, 51f, 51g, 51h, 51j, and 51k are 10 wires (e.g., stainless steel wires) that are twisted into a hollow shape as in the hollow coil body 21. The hollow coil body 51 has a cylindrical hollow shape from the distal end to the connector 9.

Further, the coil body 52 is formed such that the wires 52a, 52b, 52c, 52d, 52e, 52f, 52g, 52h, 52j, 52k, 52m, 52n, 52p, 52q, 52r, and 52s are 16 wires (e.g., stainless steel wires) that are wound around on a surface of the coil body 51 in the same direction (counterclockwise, facing to the distal end) as the hollow coil body 51. The coil body 52 also has a cylindrical hollow shape from the distal end to the connector 9.

Further, the coil body 53 is formed such that the wire 53a (e.g., a stainless steel wire) is wound around on the surfaces of the coil body 51 and the coil body 52. The hollow coil body 53 also has a cylindrical hollow shape from the distal end to the connector 9.

Each wire in the hollow coil body 51 and the coil body 52 is wound around closely (see FIG. 10). The coil body 52 is twistedly formed on the surface of the hollow coil body 51. This means that the hollow coil body 51, the coil body 52, and the closely wound portion of the coil body 53 collectively correspond to the shaft having a hollow shape with an outer diameter that is smaller at a distal end than at a proximal end. The coil body 53 provides a spirally-arranged protruding portion protruding outwardly (from the outermost surface and the outermost portion of the dilator 50) on an outer peripheral surface 51L of the hollow coil body 51 and an outer peripheral surface 52T of the coil body 52. The above spirally-arranged protruding portion has gaps between adjacent portions (adjacent windings of the wire) along an axis A of the hollow coil body 51. Further, the coil body 53 is provided at the coil body 52, which corresponds to a portion where the shaft has an increasing outer diameter.

It is noted that metal wires made of stainless steel can be used for the wires of the hollow coil body 51, the coil body 52, and the coil body 53, but they are not limited to stainless steel wires. They may be made of a superelastic alloy such as nickel-titanium. Further, they are not limited to metal wires and may be resin wires.

The dilator 50 (the multilayer body 57) can ensure the distal-end flexibility of the dilator 50 (the multilayer body 57) and can maintain the pushability and torquability of the dilator 50 (the multilayer body 57) even when the dilator 50 (the multilayer body 57) is longer and curved. Further, the screw effect of the single wire 53a extending contiguously toward the distal end from the proximal end of the coil body 53 can further be improved when the multilayer body 57 is rotated. This enables the dilator 50 to be easily advanced not only by a pushing operation but also by a rotational operation. In addition, the diameter of a pre-formed hole can be increased more easily by the coil body 53 provided at the coil body 52 which corresponds to a portion where the shaft has an increasing outer diameter.

It is noted that when the amount of gap between adjacent windings of the metal wire 53a is configured so as to be gradually reduced toward the proximal end side, the following effect can be observed: the stiffness of the dilator 50 (the multilayer body 57) along the axis direction can be gradually changed so that the dilator 50 (the multilayer body 57) can easily enter into the inside of an approach pathway even when the approach pathway meanders.

Further, a shaft (the first coil) composed of the hollow coil body 51 and the coil body 52 each including a plurality of wires wound around into a hollow shape can improve the flexibility of the shaft and the transmissibility of torque via the shaft. Further, a spirally-arranged protruding portion (the second coil) composed of the coil body 53 including a single wire wound around the outer peripheral surface 51L of the hollow coil body 51 and the outer peripheral surface 52T of the hollow coil body 52 can be easily formed, can ensure the flexibility of the distal end of the dilator 50 by virtue of the elasticity of the second coil, and can improve the torquability. Further, the wires of the hollow coil body 51 and the coil body 52 are wound in a direction opposite to the wire of the coil body 53. Therefore, even when the dilator 50 is rotated in a direction to open the hollow coil body 51 and the coil body 52, a force is applied in a direction to close the coil body 53 to prevent the opening of the hollow coil body 51 and the coil body 52. This allows a force applied to the connector 9 of the dilator 50 to be transmitted to the distal end side.

Figure 11:
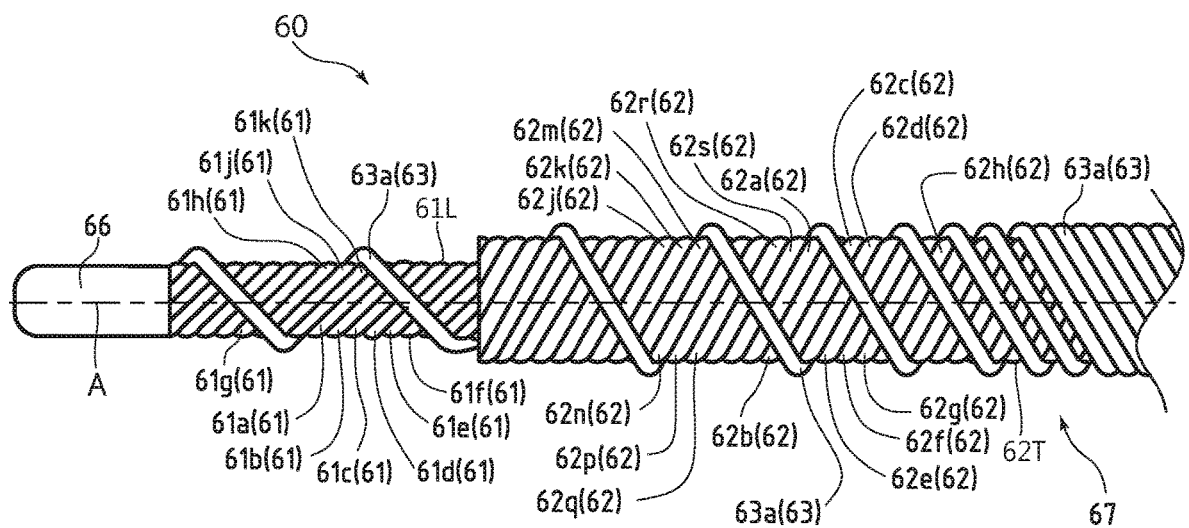
FIG. 11 shows a distal end portion of a dilator (a multilayer body) according to the disclosed embodiments.

FIG. 11 shows a distal end portion of a dilator (a multilayer body) according to the disclosed embodiments.

In FIG. 11, the left side in the figure corresponds to the front end side (the distal side) which is to be inserted into the body, and the right side corresponds to the base end side (the hand side, the proximal side) which is to be operated by an operator such as a surgeon.

In FIG. 11, a dilator 60 includes: a multilayer body 67 including a hollow coil body 61 including a plurality of wires 61a, 61b, 61c, 61d, 61e, 61f, 61g, 61h, 61j, and 61k wound around into a hollow shape; a coil body 62 proximally spaced from a distal end of the hollow coil body 61 and including a plurality of wires 62a, 62b, 62c, 62d, 62e, 62f, 62g, 62h, 62j, 62k, 62m, 62n, 62p, 62q, 62r, and 62s wound around on an outer periphery of the hollow coil body 61 in the same direction (counterclockwise, facing to the distal end) as the hollow coil body 61 (counterclockwise, facing to the distal end); and a coil body 63 including a single wire 63a wound around on the outer peripheries of the hollow coil body 61 and the coil body 62 from the distal end of the hollow coil body 61 in a direction (clockwise, facing to the distal end) opposite to the hollow coil body 62. The dilator 60 further includes a connector 9 (not shown) having a hollow shape and being connected to a proximal end of the multilayer body 67. However, the dilator 60 differs from the dilator 50 in that the multilayer body 67 of the dilator 60 has a distal-end portion 66 at the distal end of the hollow coil body 61 while the multilayer body 57 of the dilator 50 does not.

The distal-end portion 66 is formed by casting a solder material (a silver-tin solder material, a gold-tin solder material, or the like) into the distal end of the hollow coil body 61, and has a substantially cylindrical hollow shape. Further, the surface of the distal-end portion 66 is flat while the surface of the distal end of the multilayer body 57 is uneven.

The multilayer body 67 has a stepped and cylindrical hollow shape as in the multilayer body 27, but it differs from the multilayer body 27 in that the coil body 63 in the multilayer body 67 is formed integrally and continuously while the coil body 24, the coil body 25, and the coil body 23 in the multilayer body 27 are formed as separate members. That is, in the coil body 63, the single wire 63*a* is closely wound around at the proximal end side and is wound around with gaps between adjacent windings at the distal end side of the coil body 62 and the distal end side of the coil body 61.

It is noted that the hollow coil body 61 and the coil body 62 together correspond to the "shaft" and the "first coil." The portion of the coil body 63 wound around with gaps between adjacent windings corresponds to the "spirally-arranged protruding portion" and the "second coil." Further, the coil body 62 corresponds to the "portion having an increasing outer diameter."

The hollow coil body 61 is formed such that the wires 61*a*, 61*b*, 61*c*, 61*d*, 61*e*, 61*f*, 61*g*, 61*h*, 61*j*, and 61*k* are 10 wires (e.g., stainless steel wires) that are twisted into a hollow shape as in the hollow coil body 21. The hollow coil body 61 has a cylindrical hollow shape from the distal end to the connector 9.

Further, the coil body 62 is formed such that the wires 62*a*, 62*b*, 62*c*, 62*d*, 62*e*, 62*f*, 62*g*, 62*h*, 62*j*, 62*k*, 62*m*, 62*n*, 62*p*, 62*q*, 62*r*, and 62*s* are 16 wires (e.g., stainless steel wires) that are wound around on a surface of the coil body 61 in the same direction (counterclockwise, facing to the distal end) as the hollow coil body 61. The hollow coil body 62 also has a cylindrical hollow shape from the distal end to the connector 9.

Further, the coil body 63 is formed such that the wire 63*a* (e.g., a stainless steel wire) is wound around on the surfaces of the coil body 61 and the coil body 62. The hollow coil body 63 also has a cylindrical hollow shape from the distal end to the connector 9.

Each wire in the hollow coil body 61 and the coil body 62 is wound around closely (see FIG. 11). The coil body 62 is twistedly formed on the surface of the hollow coil body 61. This means that the shaft formed from the hollow coil body 61 and the coil body 62 has a hollow shape having an outer diameter that is smaller at a distal end than at a proximal end. The coil body 63 provides a spirally-arranged protruding portion protruding outwardly (the outermost surface of the dilator 60, the outermost portion) on an outer peripheral surface 61L of the hollow coil body 61 and an outer peripheral surface 62T of the coil body 62. The above spirally-arranged protruding portion has gaps between adjacent portions (adjacent windings of the wire) along an axis A of the hollow coil body 61. Further, the coil body 63 is provided at the coil body 62 which corresponds to a portion where the shaft has an increasing outer diameter.

It is noted that metal wires made of stainless steel can be used for the wires of the hollow coil body 61, the coil body 62, and the coil body 63, but they are not limited to stainless steel wires. They may be made of a superelastic alloy such as nickel-titanium. Further, they are not limited to metal wires and may be resin wires.

According to the dilator 60 (the multilayer body 67), the distal-end portion 66 having a flat surface is connected to the distal end of the multilayer body 67. This configuration can further improve insertability into a punctured portion by first pressing the dilator against the punctured portion, and then pushing and rotating the dilator inward. In addition, this configuration can ensure the distal-end flexibility of the dilator 60 (the multilayer body 67) and can improve the pushability and torquability of the dilator 60 (the multilayer body 67) even when the dilator 60 (the multilayer body 67) is longer and curved. Further, the screw effect of the single wire 63*a* extending contiguously toward the distal end from the proximal end of the coil body 63 can further be improved when the multilayer body 67 is rotated. This enables the dilator 60 to be easily advanced not only by a pushing operation but also by a rotational operation. In addition, the diameter of a pre-formed hole can be increased more easily by the coil body 63 provided at the coil body 62 which corresponds to a portion where the shaft has an increasing outer diameter.

It is noted that when the amount of gap between adjacent windings of the metal wire 63*a* is configured so as to be gradually reduced toward the proximal end side, the following effect can be observed: the stiffness of the dilator 60 (the multilayer body 67) along the axis direction can be gradually changed so that the dilator 60 (the multilayer body 67) can easily enter into the inside of an approach pathway even when the approach pathway meanders.

Further, the shaft (the first coil) composed of the hollow coil body 61 and the coil body 62 each including a plurality of wires wound around into a hollow shape can improve the flexibility of the shaft and the transmissibility of torque via the shaft. Further, a spirally-arranged protruding portion (the second coil) composed of the coil body 63 including a single wire wound around on an outer peripheral surface 61L of the hollow coil body 61 and an outer peripheral surface 62T of the hollow coil body 62 can be easily formed, can ensure the flexibility of the distal end of the dilator 60 by virtue of the elasticity of the second coil, and can improve the torquability. Further, the wires of the hollow coil body 61 and the coil body 62 are wound in a direction opposite to the wire of the coil body 63. Therefore, even when the dilator 60 is rotated in a direction to open the hollow coil body 61 and the coil body 62, a force is applied in a direction to close the coil body 63 to prevent the opening of the hollow coil body 61 and the coil body 62. This allows a force applied to the connector 9 of the dilator 60 to be transmitted to the distal end side.

Figure 12:
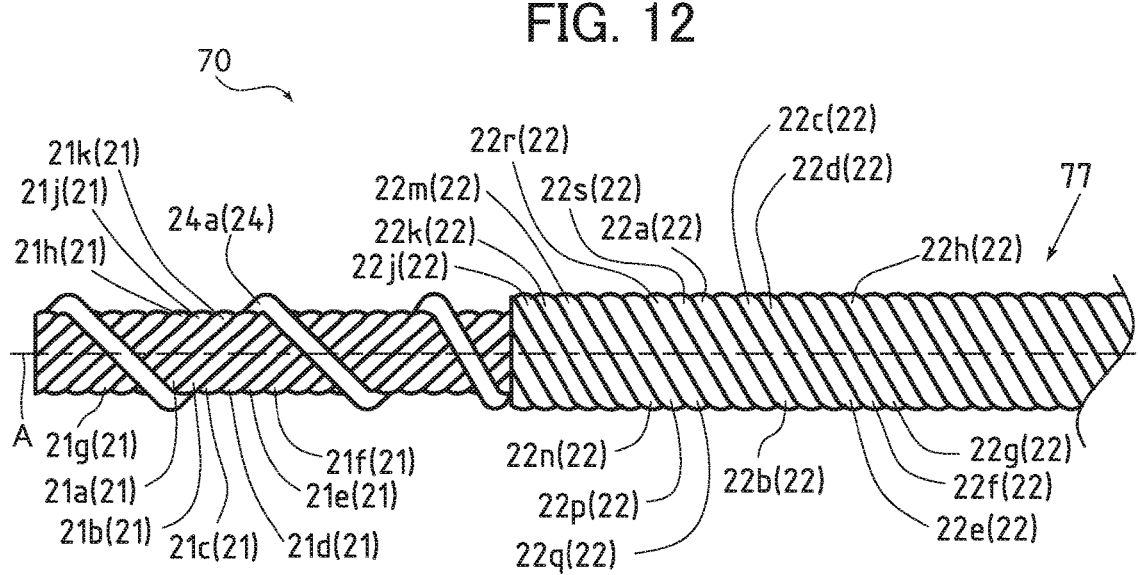
FIG. 12 shows a distal end portion of a dilator (a multilayer body) according to the disclosed embodiments.

FIG. 12 shows a distal end portion of a dilator (a multilayer body) according to the disclosed embodiments.

In FIG. 12, the left side in the figure corresponds to the front end side (the distal side) which is to be inserted into the body, and the right side corresponds to the base end side (the hand side, the proximal side) which is to be operated by an operator such as a surgeon.

In FIG. 12, a dilator 70 includes: a multilayer body 77 including a hollow coil body 21 including a plurality of wires 21*a*, 21*b*, 21*c*, 21*d*, 21*e*, 21*f*, 21*g*, 21*h*, 21*j*, and 21*k* wound around into a hollow shape; a coil body 22 proximally spaced from a distal end of the hollow coil body 21 and including a plurality of wires 22*a*, 22*b*, 22*c*, 22*d*, 22*e*, 22*f*, 22*g*, 22*h*, 22*j*, 22*k*, 22*m*, 22*n*, 22*p*, 22*q*, 22*r*, and 22*s* wound around on an outer periphery of the hollow coil body 21 in a direction (clockwise, facing to the distal end) opposite to the hollow coil body 21; and a coil body 24 including a single wire 24*a* wound around with gaps between adjacent windings on the outer periphery of the coil body 21 in a region distal to a distal end of the coil body 22. The dilator 70 further includes a connector 9 (not shown) having a hollow shape and being connected to a proximal end of the multilayer body 77.

Here, the multilayer body 77 has a stepped and cylindrical hollow shape as in the multilayer body 27 but has a two-layer structure where the coil 25 and the coil 23 are removed from the multilayer body 27.

Even in a case where the dilator 70 (the multilayer body 77) is longer and curved, the dilator 70 (the multilayer body 77) can ensure the distal-end flexibility of the dilator 70 (the multilayer body 77), can maintain the pushability and torquability of the dilator 70 (the multilayer body 77), and can enable the diameter of a pre-formed hole to be easily increased by the screw effect of the wire 24*a* upon rotation of the multilayer body 77.

However, the multilayer body 77 has a two-layer structure while the multilayer body 27 has a three-layer structure. Therefore, the multilayer body 77 may have a somewhat inferior ability for increasing the diameter of a hole as compared with the multilayer body 27.

It is noted that when the amount of gap between adjacent windings of the wire 24*a* is configured so as to be gradually reduced toward the proximal end side, the following effect can be observed: the stiffness of the dilator 70 (the multilayer body 77) along the axis direction can be gradually changed so that the dilator 70 (the multilayer body 77) can easily enter into the inside of an approach pathway even when the approach pathway meanders.

Figure 13:
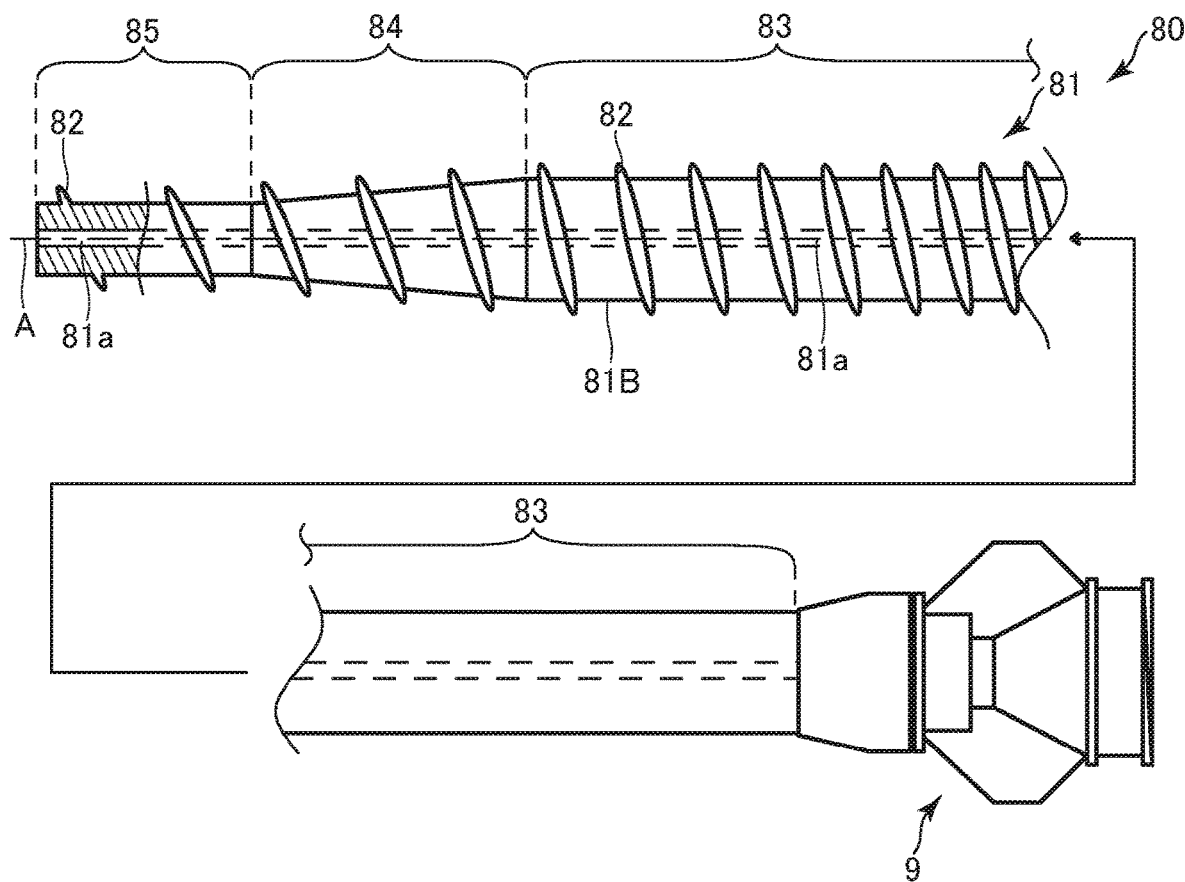
FIG. 13 show an overall view of a dilator according to the disclosed embodiments.

FIG. 13 shows an overall view of a dilator according to the disclosed embodiments.

In FIG. 13, the left side in the figure corresponds to the front end side (the distal side) which is to be inserted into the body, and the right side corresponds to the base end side (the hand side, the proximal side) which is to be operated by an operator such as a surgeon.

In FIG. 13, a dilator 80 includes a shaft 81, a spirally-arranged protruding portion 82, and a connector 9 connected to a proximal end of the shaft 81.

The shaft 81 has a hollow shape in which an inner cavity 81*a* is formed extending penetratingly from the proximal end to a distal end of the shaft 81. The shaft 81 also has a body portion 83, a tapered portion 84, and a distal-end portion 85.

There is no particular limitation for the materials of the shaft 81 and the spirally-arranged protruding portion 82 as long as they can ensure the flexibility of the tapered portion 84 and the distal-end portion 85 and have biocompatibility. For example, the following materials can be used: stainless steel; superelastic alloy materials such as nickel-titanium alloys; or synthetic resins such as polyvinyl chloride resin, urethane resin, polyolefin resin, polyamide resin, and fluororesin.

The body portion 83 is located at the proximal end side of the dilator 80, and the connector 9 is connected to a proximal end thereof. Further, the body portion 83 has a substantially constant outer diameter from the proximal end thereof through the distal end.

The tapered portion 84 is connected to the distal end of the body portion 83, extends from that distal end to the distal end side, and has a shape tapered toward the distal end side. That is, the tapered portion 84 is configured such that the outer diameter of the distal end side thereof is smaller than that of the proximal end side and corresponds to a portion having an outer diameter increasing toward the proximal end side from the distal end side of the shaft 81.

The distal-end portion 85 is connected to the distal end of the tapered portion 84 and extends from that distal end to the distal end side. Further, the distal-end portion 85 has a substantially constant outer diameter from the proximal end to the distal end thereof. As described above, the shaft 81 has a hollow shape having an outer diameter that is smaller at the distal end than at the proximal end.

The spirally-arranged protruding portion 82 is provided on an outer peripheral surface 81B of the shaft 81 so as to be protruding outwardly (from the outermost surface of the dilator 80, the outermost portion). The spirally-arranged protruding portion 82 is provided at a distal-end side portion of the body portion 83, at the tapered portion 84, and at the distal-end portion 85 and has gaps between adjacent portions along an axis A of the shaft 81. That is, the adjacent portions of the spirally-arranged protruding portion 82 are spaced from each other. The gaps are configured so as to be gradually smaller toward the proximal end side from the distal end side of the shaft 81. The spirally-arranged protruding portion 82 is integrally formed with the shaft 81 by casting or the like.

In the dilator 80, the spirally-arranged protruding portion 82 protruding outwardly is provided on the outer peripheral surface 81B of the shaft 81 and has gaps between adjacent portions along the axis A of the shaft 81. This configuration enables the dilator to be advanced not only by a conventional pushing operation but also by a rotational operation of the spirally-arranged protruding portion 82.

Further, the spirally-arranged protruding portion 82 provided at a portion having an outer diameter increasing toward the proximal end side from the distal end side of the shaft, that is, at the tapered portion 84, can easily increase the diameter of a pre-formed hole.

Further, the gaps of the spirally-arranged protruding portions 82 configured so as to be gradually smaller toward the proximal end side from the distal end side of the shaft 81 can gradually change the stiffness of the shaft 81 along the axis direction. This can ensure the flexibility of the distal end of the shaft 81 and can maintain the pushability and torquability of the shaft 81 even when the shaft 81 is longer and curved.

Figure 14:
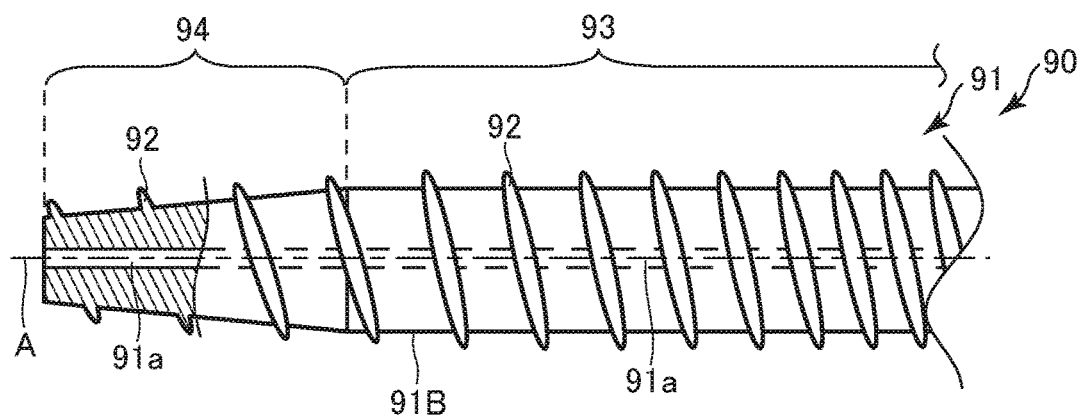
FIG. 14 shows a partial cross-sectional view of a distal-end side portion of a dilator according to the disclosed embodiments.

FIG. 14 shows a partial cross-sectional view of a distal-end side portion of a dilator according to the disclosed embodiments.

In FIG. 14, the left side in the figure corresponds to the front end side (the distal side) which is to be inserted into the body, and the right side corresponds to the base end side (the hand side, the proximal side) which is to be operated by an operator such as a surgeon.

In FIG. 14, a dilator 90 includes a shaft 91, a spirally-arranged protruding portion 92, and a connector 9 (not shown) connected to a proximal end of the shaft 91. The material(s) of the shaft 91 and the spirally-arranged protruding portion 92 is/are the same as that/those of the shaft 81 and the spirally-arranged protruding portion 82 of the dilator 80.

The shaft 91 has a hollow shape in which an inner cavity 91*a* is formed extending penetratingly from the proximal end to a distal end of the shaft 91. Further, the shaft 91 has a body portion 93 and a tapered portion 94. The dilator 90 differs from the dilator 80 in that the dilator 90 does not have a distal-end portion.

The body portion 93 and the tapered portion 94 have the same configurations as the body portion 83 and the tapered portion 84 of the dilator 80. Further, the spirally-arranged protruding portion 92 is provided on an outer peripheral surface 91B of the shaft 91 so as to be protruding outwardly (the outermost surface of the dilator 90, the outermost portion). The spirally-arranged protruding portion 92 is provided at a distal-end side portion of the body portion 93 and at the tapered portion 94 and has gaps between adjacent portions along an axis A of the shaft 91. That is, the adjacent portions of the spirally-arranged protruding portion 92 are spaced from each other. The gaps are configured so as to be gradually smaller toward the proximal end side from the distal end side of the shaft 91. The spirally-arranged protruding portion 92 is integrally formed with the shaft 91 by casting or the like. In the dilator 90, the spirally-arranged protruding portion 92 protruding outwardly is provided on the outer peripheral surface 91B of the shaft 91 and has gaps between adjacent portions along the axis A of the shaft 91 as described above. The spirally-arranged protruding portion 92 is provided at a portion having an outer diameter increasing from the distal end side to the proximal end side of the shaft, i.e., at the tapered portion 94. The gaps of the spirally-arranged protruding portions 92 are configured so as to be gradually smaller toward the proximal end side from the distal end side of the shaft 91. Therefore, the dilator 90 can produce similar effects as the dilator 80.

Figure 15:
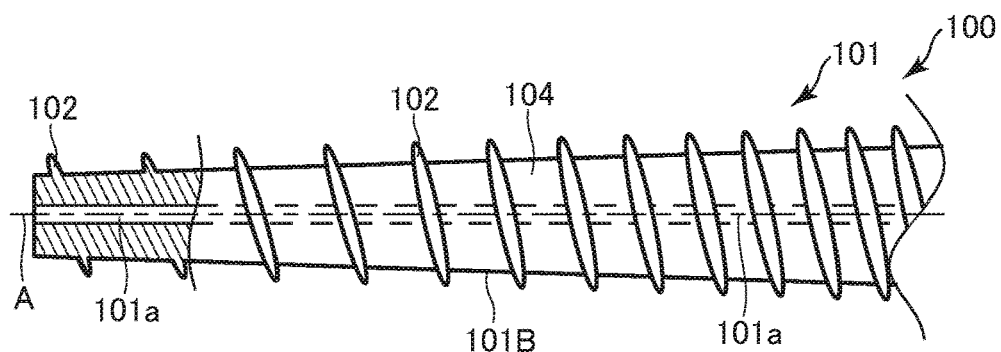
FIG. 15 shows a partial cross-sectional view of a distal-end side portion of a dilator according to the disclosed embodiments.

FIG. 15 shows a partial cross-sectional view of a distal-end side portion of a dilator according to the disclosed embodiments.

In FIG. 15, the left side in the figure corresponds to the front end side (the distal side) which is to be inserted into the body, and the right side corresponds to the base end side (the hand side, the proximal side) which is to be operated by an operator such as a surgeon.

In FIG. 15, a dilator 100 includes a shaft 101, a spirally-arranged protruding portion 102, and a connector 9 (not shown) connected to a proximal end of the shaft 101. The material(s) of the shaft 101 and the spirally-arranged protruding portion 102 is/are the same as that/those of the shaft 81 and the spirally-arranged protruding portion 82 of the dilator 80.

The shaft 101 has a hollow shape in which an inner cavity 101a is formed extending penetratingly from a proximal end to a distal end. Further, the shaft 101 has a tapered portion 104. The dilator 100 differs from the dilator 80 in that the dilator 100 does not have either a distal-end portion or a body portion. That is, the shaft 101 has a tapered shape having an outer diameter gradually decreasing from a proximal end to a distal end throughout its entire length. This means that the shaft 101 has a hollow shape having an outer diameter that is smaller at the distal end than at the proximal end.

The spirally-arranged protruding portion 102 is provided on an outer peripheral surface 101B of the shaft 101 so as to be protruding outwardly (the outermost surface of the dilator 100, the outermost portion). The spirally-arranged protruding portion 102 is provided at a distal-end side portion of the tapered portion 104 and has gaps between adjacent portions along an axis A of the shaft 101. That is, the adjacent portions of the spirally-arranged protruding portion 102 are spaced from each other. The gaps are configured so as to be gradually smaller toward the proximal end side from the distal end side of the shaft 101. The spirally-arranged protruding portion 102 is integrally formed with the shaft 101 by casting or the like.

In the dilator 100, the spirally-arranged protruding portion 102 protruding outwardly is provided on the outer peripheral surface 101B of the shaft 101 and has gaps between adjacent portions along the axis A of the shaft 101 as described above. The spirally-arranged protruding portion 102 is provided at the tapered portion 104 which corresponds to a portion having an outer diameter increasing toward the proximal end side from the distal end side of the shaft. The gaps of the spirally-arranged protruding portions 102 are configured so as to be gradually smaller toward the proximal end side from the distal end side of the shaft 101. Therefore, the dilator 100 can produce similar effects as the dilator 80.

Figure 16:
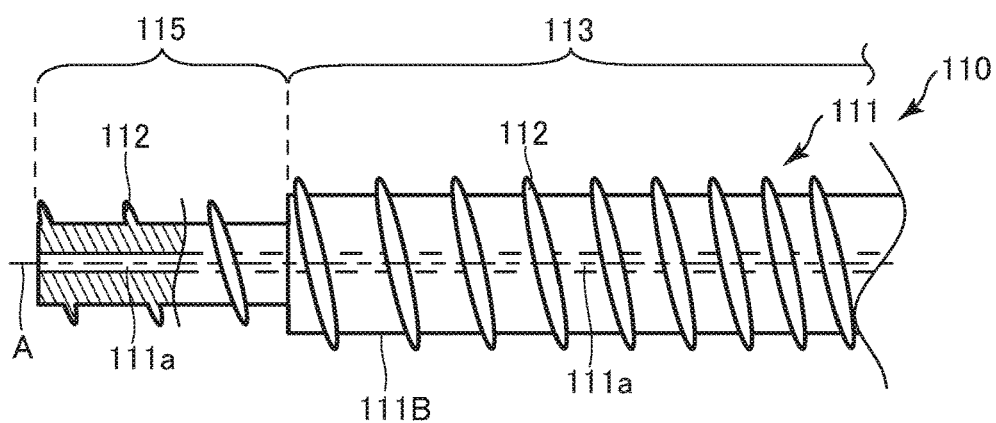
FIG. 16 shows a partial cross-sectional view of a distal-end side portion of a dilator according to the disclosed embodiments.

FIG. 16 shows a partial cross-sectional view of a distal-end side portion of a dilator according to the disclosed embodiments.

In FIG. 16, the left side in the figure corresponds to the front end side (the distal side) which is to be inserted into the body, and the right side corresponds to the base end side (the hand side, the proximal side) which is to be operated by an operator such as a surgeon.

In FIG. 16, a dilator 110 includes a shaft 111, a spirally-arranged protruding portion 112, and a connector 9 (not shown) connected to a proximal end of the shaft 111. The material(s) of the shaft 111 and the spirally-arranged protruding portion 112 is/are the same as that/those of the shaft 81 and the spirally-arranged protruding portion 82 of the dilator 80.

The shaft 111 has a hollow shape in which an inner cavity 111a is formed extending penetratingly from the proximal end to a distal end of the shaft 111. Further, the shaft 111 has a body portion 113 and a distal-end portion 115.

The body portion 113 is located at the proximal end side of the dilator 110, and the connector 9 is connected to a proximal end thereof. Further, the body portion 113 has a substantially constant outer diameter from the proximal end to the distal end thereof.

The distal-end portion 115 is connected to the distal end of the body portion 113 and extends from that distal end to the distal end side. Further, the distal-end portion 115 has a substantially constant outer diameter from the proximal end to the distal end thereof. The outer diameter of the distal-end portion 115 is smaller than that of the body portion 113, and the distal-end portion 115 is formed coaxially with the body portion 113. This means that the shaft 111 has a hollow shape having an outer diameter that is smaller at a distal end than at a proximal end. Further, the body portion 113 corresponds to a portion having an outer diameter increasing from the distal end side to the proximal end side of the shaft 111.

The spirally-arranged protruding portion 112 is provided on an outer peripheral surface 111B of the shaft 111 so as to be protruding outwardly (the outermost surface of the dilator 110, the outermost portion). The spirally-arranged protruding portion 112 is provided at a distal-end side portion of the body portion 113 and at the distal end portion 115 and has gaps between adjacent portions along an axis A of the shaft 111. That is, the adjacent portions of the spirally-arranged protruding portion 112 are spaced from each other. The gaps are configured so as to be gradually smaller toward the proximal end side from the distal end side of the shaft 111. The spirally-arranged protruding portion 112 is integrally formed with the shaft 111 by casting or the like.

In the dilator 110, the spirally-arranged protruding portion 112 protruding outwardly is provided on the outer peripheral surface 111B of the shaft 111 and has gaps between adjacent portions along the axis A of the shaft 111. This configuration enables the dilator to be advanced not only by a conventional pushing operation but also by a rotational operation of the spirally-arranged protruding portion 112.

Further, the spirally-arranged protruding portion 112 is provided at a portion having an outer diameter increasing toward the proximal end side from the distal end side of the shaft, that is, at the body portion 113. This configuration enables the diameter of a pre-formed hole to be easily increased.

Further, the gaps of the spirally-arranged protruding portions 112 configured so as to be gradually smaller toward the proximal end side from the distal end side of the shaft 111 can gradually change the stiffness of the shaft 111 at the axis A. This can ensure the flexibility of the distal end of the shaft 111 and can maintain the pushability and torquability of the shaft 111 even when the shaft 111 is longer and curved.

Hereinbefore, the embodiments of the present disclosure are described, but the present disclosure shall not be limited to these embodiments. Rather, various modifications may be made.

For example, the hollow coil body 3, the hollow coil body 21, the hollow coil body 31, the hollow coil body 41, the hollow coil body 51, and the hollow coil body 61 are described as hollow coil bodies including 10 wires in the aforementioned embodiments, but the number of wires shall not be limited to 10. The number may be one or more.

Further, the coil body 22, the coil body 42, the coil body 52, and the coil body 62 are described as coil bodies including 16 wires in the aforementioned embodiments, but the number of wires shall not be limited to 16. The number may be one or more.

Moreover, the coil body 23 and the coil body 33 are described as coil bodies including 23 wires in the aforementioned embodiments, but the number of wires shall not be limited to 23. The number may be one or more.

Moreover, the distal-end portion 6 is described to be formed by casting a solder material into the distal end of the multilayer body 17. However, the outer periphery of the coil body 5 and/or the coil body 3 in the vicinity of the distal-end portion of the multilayer body 17 may be sanded to form the distal-end portion 6 having a flat surface. This also applies to the distal-end portion 66.

Furthermore, the distal-end portion 6 is described as being fixed to the distal end of the multilayer body 17. However, similar effects may be produced by fixing a distal-end portion to the distal end of the multilayer body 27, the distal end of the multilayer body 37, the distal end of the multilayer body 47, the distal end of the multilayer body 77, the distal end of the shaft 81, the distal end of the shaft 91, the distal end of the shaft 101, or the distal end of the shaft 111.

Figure 17:
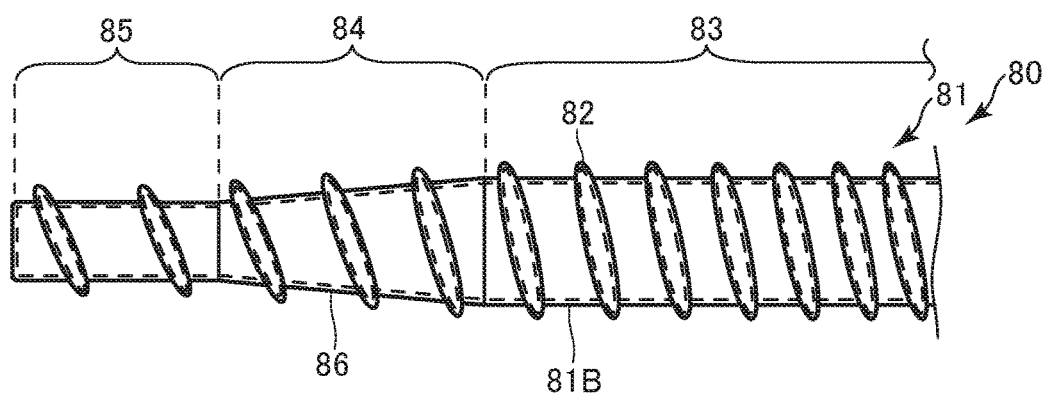
FIG. 17 shows a distal end portion of a dilator according to the disclosed embodiments.

Further, the outer peripheries of the multilayer bodies 7, 17, 27, 37, 47, 57, 67, and 77 and the shafts 81, 91, 101, and 111 and the spirally-arranged protruding portions 82, 92, 102, and 112 may be coated with a resin(s). For example, the outer peripheries of the shaft 81 and the spirally-arranged protruding portion 82 of the dilator 80 may be coated with a resin 86 as shown in FIG. 17. The resin 86 can improve slidability to prevent damage to living body tissue. When the outer periphery of the shaft 81 is coated with the resin 86, a portion where the body portion 83, the tapered portion 84, and the distal-end portion 85 are coated with the resin 86 corresponds to the shaft 81, and a portion protruding outwardly from the outer peripheral surface 81B of the shaft 81 corresponds to the spirally-arranged protruding portion 82. Examples of the resin 86 include, for example, biocompatible resin materials such as polyamide resin and fluororesin, or hydrophilic coating materials. The resin 86 may have a thickness of, for example, 0.1 μm to 300 μm.

Further, the spirally-arranged protruding portions 82, 92, 102, and 112 are configured to have gaps between adjacent portions along the axis A, the gaps becoming gradually smaller toward the proximal end side from the distal end side of the shaft 81. However, the gaps may be evenly spaced. Moreover, the shafts 81, 91, 101, and 111 and the spiral protruding portions 82, 92, 102, and 112 are integrally formed but may be formed separately.

The shaft may have various types of coating on the side of the surface thereof (including a portion between the shaft and the spirally-arranged protruding portion) other than or in addition to the resin 86 shown in FIG. 17. Examples of the coating include, for example, a protective film on the surface of the shaft (representative example: a plating film), an underlying film for improving adhesiveness between the shaft and the spirally-arranged protruding portion, and the like.

Preferably, the spirally-arranged protruding portions are not configured to serve as a blade. The dilators are intended for expanding a hole pre-formed on a target object (for example, the wall of a digestive tract such as the patient's stomach). Therefore, if the spirally-arranged protruding portion serves as a blade, living tissue at the inner surface of the hole may be damaged.

For this reason, the spirally-arranged protruding portion preferably does not have a sharp edge at an end portion at a radially outer side of the shaft in a cross-section (for example, a cross-section perpendicular to the spiral direction of the spirally-arranged protruding portion 82 as shown in FIG. 13). That is, the above end portion preferably has an area having a shape including an obtuse angle or a curve (for example, a curve constituting a part of a circle or an ellipse). Thus, the spirally-arranged protruding portion is configured so as not to cut living tissue when dilating a hole pre-formed on a target object.

What is claimed is:

1. A dilator comprising:
    a hollow shaft having an outer diameter that is smaller at a distal end of the shaft than at a proximal end of the shaft;
    a spirally-arranged protruding portion provided on an outer peripheral surface of the shaft and forming an exterior surface of the dilator, the spirally-arranged protruding portion protruding radially outward from the shaft; and
    a grip portion connected to the proximal end of the shaft, wherein:
    the spirally-arranged protruding portion has gaps between adjacent portions of the spirally-arranged protruding portion along a longitudinal axis of the shaft,
    the shaft includes a first coil having one or more first wires wound around into a hollow shape, and
    the spirally-arranged protruding portion includes a second coil having one or more second wires wound around the outer peripheral surface of the shaft.

2. The dilator according to claim 1, wherein the second coil is formed of a single wire that is wound around on the outer peripheral surface of the shaft.

3. The dilator according to claim 1, wherein at a proximal end side of the shaft, adjacent windings of the one or more second wires are in contact with each other, and at a distal end side of the shaft, gaps are present between adjacent windings of the one or more second wires, the distal end side of the shaft including a portion having a tapered shape.

4. The dilator according to claim 1, wherein:
    the first coil includes a plurality of the first wires wound around into a hollow shape tapered toward the distal end of the shaft, and
    the second coil includes a single second wire wound around on a surface of the first coil, and
    at a proximal end side of the shaft, adjacent windings of the second wire are in contact with each other, and at a distal end side of the shaft in which the first wires are wound around into the hollow tapered shape, gaps are present between adjacent windings of the second wire.

5. The dilator according to claim 4, wherein a length of the gap between the adjacent windings of the second wire in a direction of the longitudinal axis is gradually reduced at a cylindrical portion of the shaft between the proximal end side of the shaft and the distal end side of the shaft.

6. The dilator according to claim 4, wherein:
the shaft further includes a third coil including a plurality of third wires wound around on an outer periphery of the first coil, a distal end of the second coil being spaced proximally from a distal end of the first coil;
the first coil includes a plurality of the first wires wound around into a hollow shape; and
the second coil has a single second wire wound around on the outer periphery of the first coil in a region distal to the distal end of the third coil, the second coil having gaps between adjacent windings of the second wire.

7. The dilator according to claim 6, wherein the second coil is integrally formed with the third coil.

8. The dilator according to claim 6, wherein the shaft further comprises:
a fourth coil including a plurality of fourth wires wound around on an outer periphery of the third coil, a distal end of the fourth coil being spaced proximally from the distal end of the third coil, and
a fifth coil including a single fifth wire wound around on the outer periphery of the third coil in a region distal to the distal end of the fourth coil, the fifth wire being wound in the same direction as the second wire, and the fifth coil having gaps between adjacent windings of the fifth wire.

9. The dilator according to claim 8, wherein the fifth coil is integrally formed with the fourth coil.

10. The dilator according to claim 9, wherein a length of the gap between adjacent windings of the second wire in the second coil, and a length of the gap between adjacent windings of the fourth wire in the fourth coil are gradually reduced toward the proximal end of the shaft.

11. The dilator according to claim 1, wherein a length of the dilator is 1600 mm or more.

12. A dilator comprising:
a hollow shaft having an outer diameter that is smaller at a distal end of the shaft than at a proximal end of the shaft;
a spirally-arranged protruding portion provided on an outer peripheral surface of the shaft, the spirally-arranged protruding portion protruding radially outward from the shaft; and
a grip portion connected to the proximal end of the shaft, wherein:
the spirally-arranged protruding portion has gaps between adjacent portions of the spirally-arranged protruding portion along a longitudinal axis of the shaft,
the shaft includes a first layer body having a plurality of first wires wound around into a hollow shape tapered toward the distal end of the shaft, and
the spirally-arranged protruding portion includes a second layer body having a single second wire wound around on a surface of the first layer body.

13. The dilator according to claim 12, wherein the second wire is in contact with the first layer body continuously from a proximal end of the second wire to a distal end of the second wire.

* * * * *